United States Patent
Upadhyay et al.

(10) Patent No.: US 12,361,327 B1
(45) Date of Patent: Jul. 15, 2025

(54) SYSTEMS AND METHODS FOR TRAINING MACHINE LEARNING MODELS USING UNLABELED ELECTROCARDIOGRAM DATA

(71) Applicant: Anumana, Inc., Cambridge, MA (US)

(72) Inventors: Uddeshya Upadhyay, Bengaluru (IN); Mayank Sharma, Bangalore (IN); Sairam Bade, Suryapet (IN); Ashim Prasad, Bangalore (IN); Rakesh Barve, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/665,932

(22) Filed: May 16, 2024

(51) Int. Cl.
G06N 20/00 (2019.01)
A61B 5/0245 (2006.01)

(52) U.S. Cl.
CPC ........... G06N 20/00 (2019.01); A61B 5/0245 (2013.01)

(58) Field of Classification Search
CPC .......... G06N 3/045; G06N 3/04; G06N 3/044; G06N 3/08; G06N 20/00; G06N 3/0464; A61B 5/7264; A61B 5/349; A61B 5/366; A61B 5/339; A61B 5/7267; A61B 5/361; A61B 5/0006; A61B 5/7275; A61B 5/318; A61B 5/363; A61B 5/0022; A61B 5/346; A61B 5/352; A61B 5/364; A61B 5/7221; A61B 5/28; A61B 5/316; A61B 5/0816; A61B 5/14542; A61B 5/7203; A61B 5/02416; A61B 5/02427; A61B 5/6801; A61B 5/6846; A61B 5/0245; A61B 5/282;

(Continued)

(56) References Cited

U.S. PATENT DOCUMENTS

2022/0084679 A1* 3/2022 Lee .................. G06N 3/088
2023/0306267 A1 9/2023 Jacob Banville et al.

FOREIGN PATENT DOCUMENTS

CN 116385837 A 7/2023
CN 116843830 A 10/2023
KR 20230133230 A 9/2023

OTHER PUBLICATIONS

"Vectorcardiographic diagnostic & prognostic information derived from the 12-lead electrocardiogram: Historical review and clinical perspective" Man et al (Year: 2015).*

(Continued)

*Primary Examiner* — Luis A Sitiriche
(74) *Attorney, Agent, or Firm* — Caldwell Intellectual Property Law

(57) ABSTRACT

A system for training machine learning models with unlabeled electrocardiogram signals, the system including a memory containing instructions configurating a processor to receive a plurality of electrocardiogram (ECG) data in a textual format, create one or more overlapping temporal patches from the plurality of ECG data, mask at least one temporal patch from the one or more overlapping temporal patches, pretrain an ECG machine learning model to predict the at least one masked temporal patch from the one or more overlapping temporal patches, adjust one or more parameter values of the ECG machine learning model as a function of the at least one predicted masked temporal patch and the at least one masked temporal patch and train the ECG machine learning model as a function of the one or more parameter values and a labeled set of ECG training data.

18 Claims, 8 Drawing Sheets

(58) Field of Classification Search
CPC ........... A61B 5/341; A61B 5/36; A61B 5/725; A61B 5/7253; A61B 5/742; A61B 5/1102; A61B 5/1118; A61B 5/333; A61B 5/4833; A61B 5/7282; A61B 5/7405; A61B 5/02405; A61B 5/02438; A61B 5/0535; A61B 5/14532; A61B 5/332; A61B 5/347; A61B 5/353; A61B 5/355; A61B 5/358; A61B 5/6805; A61B 5/6823; A61B 5/6831; A61B 5/7235; A61B 5/7285; A61B 2503/02; A61B 2503/40; A61B 2560/0412; A61B 2562/0219; A61B 2562/028; A61B 5/0024; A61B 5/02007; A61B 5/02055; A61B 5/022; A61B 5/024; A61B 5/02411; A61B 5/1032; A61B 5/1116; A61B 5/14539; A61B 5/256; A61B 5/259; A61B 5/29; A61B 5/303; A61B 5/327; A61B 5/33; A61B 5/344; A61B 5/35; A61B 5/367; A61B 5/389; A61B 5/486; A61B 5/6824; A61B 5/6828; A61B 5/6832; A61B 5/6898; A61B 5/7225; A61B 5/7278; A61B 5/7425; A61B 5/7445; A61B 5/7465; A61B 5/7475; G16H 50/20; G16H 50/30; G16H 40/67; G16H 40/63; G16H 50/70; G16H 10/60; G16H 20/30; G16H 20/40; G16H 30/20; G16H 15/00; G16H 30/40; G16H 40/60; G16H 50/50; G16H 20/10; G16H 40/20; G16H 80/00; G06F 21/6245

See application file for complete search history.

(56) References Cited

OTHER PUBLICATIONS

"Inter-Patient Congestive Heart Failure Detection Using ECG-Convolution-Vision Transformer Network" Liu et al (Year: 2022).*

* cited by examiner

SYSTEMS AND METHODS FOR TRAINING MACHINE LEARNING MODELS USING UNLABELED ELECTROCARDIOGRAM DATA

FIELD OF THE INVENTION

The present invention generally relates to the field of machine learning models. In particular, the present invention is directed to systems and methods of training machine learning models using unlabeled electrocardiogram data.

BACKGROUND

Current systems used for self-supervised machine learning processes of electrocardiogram data utilize image transformation and other intensive processing techniques. Such techniques require a larger memory footprint and make the machine learning models less efficient due to the vast amount of processing power required. In addition, current self-supervised machine learning processes require electrocardiogram signals to first be converted into images, thereby making the process even less efficient.

SUMMARY OF THE DISCLOSURE

In an aspect, a system for training machine learning models with unlabeled electrocardiogram signals is described. The system includes at least a processor and a memory communicatively connected to the at least a processor. The memory contains instructions configurating the at least a processor to receive a plurality of electrocardiogram (ECG) data in a textual format, create one or more overlapping temporal patches from the plurality of ECG data, mask at least one temporal patch from the one or more overlapping temporal patches, pretrain an ECG machine learning model to predict the at least one masked temporal patch from the one or more overlapping temporal patches, adjust one or more parameter values of the ECG machine learning model as a function of the at least one predicted masked temporal patch and the at least one masked temporal patch and train the ECG machine learning model as a function of the one or more parameter values and a labeled set of ECG training data.

In another aspect, a method for training machine learning models with unlabeled electrocardiogram signals is described. The method including receiving, by at least a processor, a plurality of electrocardiogram (ECG) data in a textual format, creating, by the at least a processor, one or more overlapping temporal patches from the plurality of ECG data, masking, by the at least a processor, at least one temporal patch from the one or more overlapping temporal patches, pretraining, by the at least a processor, an ECG machine learning model to predict the at least one masked temporal patch from the one or more overlapping temporal patches, adjusting, by the at least a processor, one or more parameter values of the ECG machine learning model as a function of the at least one predicted masked temporal patch and the at least one masked temporal patch and training, by the at least a processor, the ECG machine learning model as a function of the one or more parameter values and a labeled set of ECG training data.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Deep learning based methods have been used to analyze the (Electrocardiogram) ECG signals, however, oftentimes such methods are trained from scratch for a particular problem (e.g. disease classification from the ECGs). This paradigm is limited by the amount of "labeled" data one has (in this context, labeled data would correspond to having both the ECG signal and the corresponding disease labels). Such labeling or annotation efforts may not always be feasible on a large scale. In contrast, "self-supervised learning (SSL)" paradigm firsts learns to extract the meaningful general-purpose representation of the data points using a large amount of "unlabeled" data, and then fine-tune it for a particular use case (e.g. disease classification) using limited amounts of "labeled" data. While such methods have been extensively designed and studied for modalities such as images and text, there is not much literature on such SSL techniques designed for signals, such as ECGs. Some of the recent works leverage existing SSL techniques by plotting ECGs as images and applying the image-based SSL model. But this is highly inefficient as images would need much larger memory footprint and neural networks, whereas the ECG signal itself is low dimensional.

Figure 1:
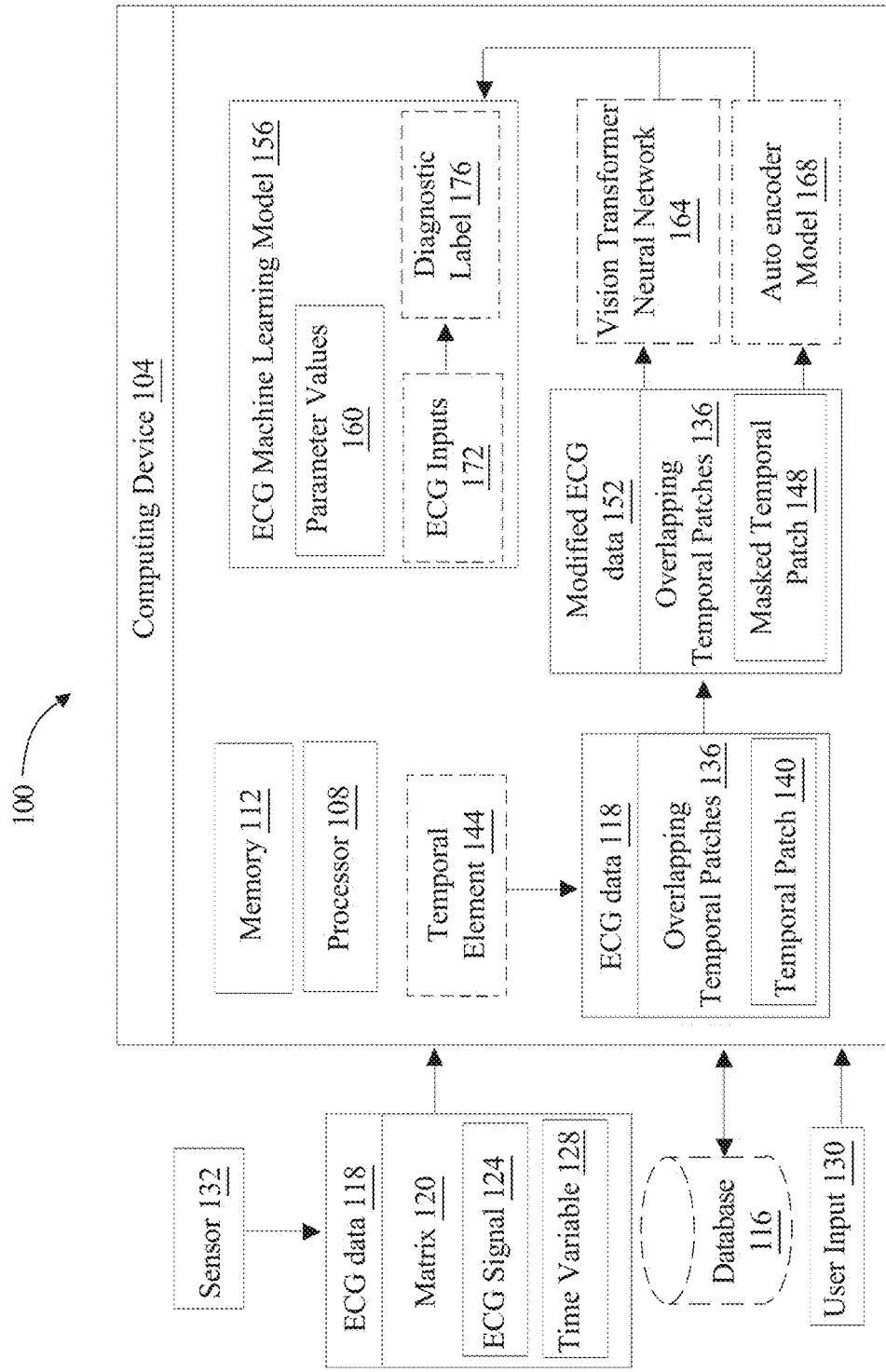
FIG. 1 is an exemplary embodiment of a system for training machine learning models with unlabeled electrocardiogram signals in accordance with the subject disclosure.

Referring now to FIG. 1, a system 100 for training machine learning models using unlabeled electrocardiogram data is described. System 100 includes a computing device

104. System 100 includes a processor 108. Processor 108 may include, without limitation, any processor 108 described in this disclosure. Processor 108 may be included in a and/or consistent with computing device 104. In one or more embodiments, processor 108 may include a multi-core processor. In one or more embodiments, multi-core processor may include multiple processor cores and/or individual processing units. "Processing unit" for the purposes of this disclosure is a device that is capable of executing instructions and performing calculations for a computing device 104. In one or more embodiments, processing units may retrieve instructions from a memory, decode the data, secure functions and transmit the functions back to the memory. In one or more embodiments, processing units may include an arithmetic logic unit (ALU) wherein the ALU is responsible for carrying out arithmetic and logical operations. This may include, addition, subtraction, multiplication, comparing two data, contrasting two data and the like. In one or more embodiments, processing unit may include a control unit wherein the control unit manages execution of instructions such that they are performed in the correct order. In none or more embodiments, processing unit may include registers wherein the registers may be used for temporary storage of data such as inputs fed into the processor and/or outputs executed by the processor. In one or more embodiments, processing unit may include cache memory wherein memory may be retrieved from cache memory for retrieval of data. In one or more embodiments, processing unit may include a clock register wherein the clock register is configured to synchronize the processor with other computing components. In one or more embodiments, processor 108 may include more than one processing unit having at least one or more arithmetic and logic units (ALUs) with hardware components that may perform arithmetic and logic operations. Processing units may further include registers to hold operands and results, as well as potentially "reservation station" queues of registers, registers to store interim results in multi-cycle operations, and an instruction unit/control circuit (including e.g. a finite state machine and/or multiplexor) that reads op codes from program instruction register banks and/or receives those op codes and enables registers/arithmetic and logic operators to read/output values. In one or more embodiments, processing unit may include a floating-point unit (FPU) wherein the FPU is configured to handle arithmetic operations with floating point numbers. In one or more embodiments, processor 108 may include a plurality of processing units wherein each processing unit may be configured for a particular task and/or function. In one or more embodiments, each core within multi-core processor may function independently. In one or more embodiments, each core within multi-core processor may perform functions in parallel with other cores. In one or more embodiments, multi-core processor may allow for a dedicated core for each program and/or software running on a computing system. In one or more embodiments, multiple cores may be used for a singular function and/or multiple functions. In one or more embodiments, multi-core processor may allow for a computing system to perform differing functions in parallel. In one or more embodiments, processor 108 may include a plurality of multi-core processors. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing devices operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory 112 between computing devices. Computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may perform determinations, classification, and/or analysis steps, methods, processes, or the like as described in this disclosure using machine-learning processes. A "machine-learning process," as used in this disclosure, is a process that automatedly uses a body of data known as "training data" and/or a "training set" (described further below in this disclosure) to generate an algorithm that will be performed by a Processor module to produce outputs given data provided as inputs; this is in contrast to a non-machine learning software program where the commands to be executed are determined in advance by a user and written in a programming language. A machine-learning process may utilize supervised, unsupervised, lazy-learning processes and/or neural networks, described further below.

With continued reference to FIG. 1, system 100 includes a memory 112 communicatively connected to processor 108, wherein the memory 112 contains instructions configuring processor 108 to perform any processing steps as described herein. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device 104. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 112 may include a primary memory and a secondary memory. "Primary memory" also known as "random access memory" (RAM) for the purposes of this disclosure is a short-term storage device in which information is processed. In one or more embodiments, during use of computing device 104, instructions and/or information may be transmitted to primary memory wherein information may be processed. In one or more embodiments, information may only be populated within primary memory while a particular software is running. In one or more embodiments, information within primary memory is wiped and/or removed after computing device 104 has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 108 may access the information from primary memory.

Still referring to FIG. 1, System 100 may include a database 116. Database may include a remote database 116. Database 116 may be implemented, without limitation, as a relational database, a key-value retrieval database such as a NOSQL database, or any other format or structure for use as database that a person skilled in the art would recognize as suitable upon review of the entirety of this disclosure. Database may alternatively or additionally be implemented using a distributed data storage protocol and/or data structure, such as a distributed hash table or the like. Database 116 may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, system 100 may include and/or be communicatively connected to a server, such as but not limited to, a remote server, a cloud server, a network server and the like. In one or more embodiments. In one or more embodiments, computing device 104 may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by system computing device 104. In one or more embodiments, computing device 104 may transmit processes to server wherein computing device 104 may conserve power or energy.

With continued reference to FIG. 1, processor is configured to receive electrocardiogram data 118. "Electrocardiogram data" for the purposes of this disclosure is information associated with electrocardiogram signals. In one or more embodiments, electrocardiogram data 118 may include a matrix 120 having a plurality of electrocardiogram signals 124 and/or associated time variables 128. A "matrix" for the purposes of this disclosure is an array of numbers or characters arranged in rows or columns which are used to represent an object or properties of the object. For example, and without limitation, a matrix may be used to describe linear equations, differential equations, in a two-dimensional format. In another non limiting example, a matrix may be used to create graphs based on data points, generate statistical models and the like. In one or more embodiments, matrix 120 may include a plurality of electrocardiogram signals associated with a plurality of time variables 128. As used in the current disclosure, a "electrocardiogram signal" is a signal representative of electrical activity of heart. The ECG signal 124 may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves may provide information about the duration and regularity of various phases of the cardiac cycle. The ECG signal 124 may help diagnose various heart conditions, such as arrhythmias, myocardial infarction (heart attack), conduction abnormalities, and electrolyte imbalances. In one or more embodiments, ECG signals 124 may be received by one or more electrodes connected to the skin of an individual. In one or more embodiments, ECG signals 124 may represent depolarization and repolarization occurring in the heart. In one or more embodiments, ECG signals 124 may be captured periodically. For example, and without limitation, every second, every millisecond and the like. In one or more embodiments, each ECG signal 124 may contain an associated time variable 128. "Time variable" for the purposes of this disclosure is information indicating the time at which a particular ECG signal 124 was received. For example, and without limitation, time variable 128 may include, 5 ms, 10 ms, 15 ms and the like. In one or more embodiments, each ECG signal 124 may contain a time variable 128. In one or more embodiments, time variable 128 may increase in given increments, such as for example., in increments of 5 ms, wherein a first time variable 128 may include 5 ms and a second time variable 128 may include 10 ms. In one or more embodiments, a combination of a plurality of ECG signals 124 and correlated time variable 128 may be used to generate a graph illustrating the heart functions of an individual. In one or more embodiments, matrix 120 may include a plurality of ECG signals 124 and correlated time variable 128 during a given time frame such as, for example, over the span of a second, a minute, an hour, and the like. In one or more embodiments, ECG signals 124 may be captured as voltages, such as millivolts or microvolts.

With continued reference to FIG. 1, the plurality of electrocardiogram signals may capture a temporal view of cardiac electrical activities. A "temporal view," as used in the current disclosure, refers to the analysis and visualization of heart-related events and phenomena over time. A temporal view may include patterns, changes, and dynamics of cardiac activity over time. A temporal view may include information surrounding the rhythm of the heart, including the regularity or irregularity of heartbeats. It allows for the identification of various rhythm abnormalities such as tachycardia (fast heart rate), bradycardia (slow heart rate), or arrhythmias (irregular heart rhythms). A temporal view of cardiac activities in three dimensions may refer to a visualization that represents the temporal evolution of cardiac events or phenomena in a three-dimensional space. It provides a comprehensive understanding of how various cardiac activities change over time. The ECG signal 124 may move through the 3D space of the heart over time. The signal does not just move forward in time, it also moves through the physical space of the heart, from SA node through atria, to AV node, and then through the ventricles. Such movement of the electrical signal through the heart's physical space over time can be referred to as "spatiotemporal excitation and propagation" which could be captured by plurality of ECG signals 124. It is essentially a way of observing and analyzing the timing and sequence of the heart's electrical activity as it moves through the physical structure of the heart. In the current case the dimensions may include axis representing time, spatial dimensions, and cardiac activity. By combining the temporal, spatial, and cardiac activity dimensions, the temporal view of cardiac activities in three dimensions allows for a comprehensive visualization and analysis of dynamic changes occurring within the heart. It can be used to study phenomena like electrical conduction, ventricular wall motion, valve function, blood flow dynamics, or the interaction between different regions of the heart. This visualization approach provides valuable insights into the complex temporal dynamics of cardiac activities and aids in understanding cardiac function, pathology, and treatment evaluation.

With continued reference to FIG. 1, matrix 120 and/or ECG signals 124 may be received through one or more input devices 130. "Input device" for the purposes of this disclosure is a device capable of transmitting information to computing device. For example, and without limitation, input device 130 may include a keyboard, a mouse, a touchscreen, a smartphone, a network server, a sensor 132 and the like. In one or more embodiments, input device 130 may include a sensor 132. In one or more embodiments, matrix 120 and/or ECG signals 124 may be received by input device 130 and/or sensor 132. As used in this disclosure, a "sensor" is a device that is configured to detect an input and/or a phenomenon and transmit information related to the detection. Sensor 132 may detect a plurality of data. A plurality of data detected by sensor 132 may include, but is not limited to, electrocardiogram signals, heart rate, blood pressure, electrical signals related to the heart, time variables 128 associated with captured data and the like. In one or more embodiments, and without limitation, sensor 132 may include a plurality of sensors 132. In one or more embodiments, and without limitation, sensor 132 may include one or more electrodes, and the like. Electrodes used for an electrocardiogram (ECG) are small sensors 132 or conductive patches that are placed on specific locations on the body to detect and record the electrical signals generated by the heart. Senor may serve as the interface between the body and the ECG machine, allowing for the measurement and recording of the heart's electrical activity. A plurality of sensors 132 may include 10 electrodes used for a standard 12-lead ECG, placed in specific positions on the chest and limbs of the patient. These electrodes are typically made of a conductive material, such as metal or carbon, and are connected to lead wires that transmit the electrical signals to the ECG machine for recording. In one or more embodiments, plurality of ECG signals 124 may be associated with a 12-lead electrocardiogram. Proper electrode placement is crucial to ensure accurate signal detection and recording. In one or more embodiments, sensors 132 may include wireless sensors 132 wherein data may be received from sensor 132 to computing device wirelessly. In one or more embodiments, wireless sensors 132 may include Bluetooth enabled ECG sensors, RFID ECG sensors, Wi-Fi enabled ECG sensors and the like. In one or more embodiments, wireless sensors 132 may allow for receipt of data from a distance. In one or more embodiments, wireless sensors 132 may allow for a machine or system to receive data without wires connecting the sensors 132 to computing device. In one or more embodiments, the presence of wires from sensors 132 to computing device may obstruct medical personnel from conducting one or more medical treatment procedures.

With continued reference to FIG. 1, the plurality of sensors 132 may be placed on each limb, wherein there may be at least one sensor on each arm and leg. These sensors may be labeled I, II, III, V1, V2, V3, V4, V5, V6, and the like. For example, Sensor I may be placed on the left arm, Sensor II may be placed on the right arm, and Sensor III may be placed on the left leg. Additionally, a plurality of sensors may be placed on various portions of the patient's torso and chest. For example, a sensor V1 may be placed in the fourth intercostal space at both the right sternal borders and sensor V2 may be fourth intercostal space at both the left sternal borders. A sensor V3 may also be placed between sensors V2 and V4, halfway between their positions. Sensor V4 may be placed in the fifth intercostal space at the midclavicular line. Sensor V5 may be placed horizontally at the same level as sensor V4 but in the anterior axillary line. Sensor V6 may be placed horizontally at the same level as V4 and V5 but in the midaxillary line. In one or more embodiments, each sensor and/or lead may contain a set of electrical signals, wherein matrix 120 may include ECG signals 124 associated with each lead and/or sensor.

With continued reference to FIG. 1, the plurality of sensors may include augmented unipolar sensors. These sensors may be labeled as aVR, aVL, and aVF. These sensors may be derived from the limb sensors and provide additional information about the heart's electrical activity. These leads are calculated using specific combinations of the limb leads and help assess the electrical vectors in different orientations. For example, aVR may be derived from Sensor II and Sensor III. In another example, aVL may be derived from sensor I and Sensor III. Additionally, aVF may be derived from Lead I and Lead II. The combination of limb sensors, precordial sensors, and augmented unipolar sensors allows for a comprehensive assessment of the heart's electrical activity in three dimensions. These leads capture the electrical signals from different orientations, which are then transformed into transformed coordinates to generate vectorcardiogram (VCG) representing magnitude and direction of electrical vectors during cardiac depolarization and repolarization. Transformed coordinates may include one or more a Cartesian coordinate system (x, y, z), polar coordinate system (r, θ), cylindrical coordinate system (ρ, φ, z), or spherical coordinate system (r, θ, φ). In some cases, transformed coordinates may include an angle, such as with polar coordinates, cylindrical coordinates, and spherical coordinates. In some cases, VCG may be normalized thus permitting full representation with only angles, i.e., angle traversals. In some cases, angle traversals may be advantageously processed with one or more processes, such as those described below and/or spectral analysis.

With continued reference to FIG. 1, in one or more embodiments, sensor 132 may include surface electrodes wherein the surface electrodes may be placed above the skin of a user and used to detect electrical impulses. In one or more embodiments, sensor 132 may further include a wearable ECG monitor wherein the wearable ECG monitor may be wrapped around a limb of the individual and used to detect electrical impulses. In one or more embodiments, sensor 132 may further include a Holter monitor, subdermal needle electrodes, and/or any other sensing device capable of receiving electrical signals.

With continued reference to FIG. 1, matrix 120 may include a plurality of ECG signals 124 captured at discrete time intervals. In one or more embodiments, matrix 120 may be generated and/or received in a digital imaging and communications in medicine (DICOM) Format, a CSV format, as a spread sheet containing cells for each datum and the like. In one or more embodiments, computing device may receive data in a raw format wherein the data may be converted into a matrix.

With continued reference to FIG. 1, ECG signals 124 received from each sensor 132 may be referred to as an 'ECG set.' In one or more embodiments, an ECG set may include ECG signals 124 captured from a singular sensor 132 over a given period of time. In one or more embodiments, ECG data 118 may include a plurality of ECG sets wherein each ECG sets may correspond to a differing input device differing sensor 132 and the like in contact with an individual. In one or more embodiments, each ECG set may correspond to a different surface electrode in contact with an individual. In one or more embodiments, ECG data 118 may include ECG sets wherein ECG sets include similar timeframes in which ECG signals 124 are captured. For example, and without limitation, an 8-lead system 100 may include 8 ECG sets wherein each ECG set corresponds to a particular lead.

With continued reference to FIG. 1, processor 108 may be configured to receive plurality of ECG data 118. In one or more embodiments, ECG data 118 may be received in textual format. A "Textual format" for the purposes of this disclosure is a format in which a set of data is represented by characters, numbers or any other alphanumeric representations. For example, and without limitation, a set of data may be said to be in textual format in instances in which the contents of the file contain only characters of readable material. In one or more embodiments, data in textual format may be contrasted with an image, video and the like. In one or more embodiments, data within a textual format may include machine-readable alphanumeric characters. In one or more embodiments, data within a textual format may include data such as .txt, .docx, .xlsx and the like. In one or more embodiments, ECG data 118 may be received in textual format wherein ECG data 118 may include textual data corresponding to Leads and corresponding voltage signals of the leads.

In one or more embodiments, ECG data 118 may include matrix 120 and/or an array of data wherein matrix 120 may include matrix 120 of size N×T, where N is the number of leads in the ECG and T is the number of voltage signals recorded in that ECG. In one or more embodiments, 'T' will depend on the frequency of the acquired ECG data 118 (referred to herein as 'f') and the length of the signal in seconds (referred to herein as 'S'), i.e., T=f*S. In one or more embodiments, matrix 120 may include a two dimensional array having size of N×T wherein N may denote the number and/or particular leads and T may denote the voltage signals. In one or more embodiments, ECG data 118 may be received in a 3-dimesnional array of N×T×S wherein s may denote the seconds and/or time corresponding to each voltage signal. In one or more embodiments, ECG data 118 may include a matrix 120 having one or more leads and voltage signals associated with each of the one or more leads. In an embodiment, each lead may be configured to receive voltage signals from a patient wherein ECG data 118 may include voltage signals from each lead on the patient. In one or more embodiments, leads may include any leads as described above. In one or more embodiments, each ECG data 118 may include data received from multiple leads in contact with a patient. In one or more embodiments, processor 108 may be configured to receive a plurality of ECG data 118 wherein each ECG data 118 is associated with a particular individual and/or medical patient. In one or more embodiments, ECG data 118 may contain voltage signals over a given period of time and/or ECG signals 124. In one or more embodiments, each voltage signal within ECG data 118 may contain corresponding time variable 128 (as described above) wherein time variable 128 denotes the time at which the particular voltage signal was received. In an embodiment, matrix 120 may include an array for each lead wherein the array contains voltage signals and time variables 128 associated with the voltage signals. In one or more embodiments, sensors 132 associated with each lead may be configured to receive voltage signals and corresponding time variables 128. In one or more embodiments, ECG data 118 may be received from a plurality of patients, from a database 116, from a web using a web crawler and the like. In one or more embodiments, each set of ECG data 118 may correspond to a particular individual and/or patient. In one or more embodiments, ECG data 118 may contain ECG signals 124 received from each sensor 132 of a plurality of sensors 132 that were in contact with a patient. In one or more embodiments, the sensors 132 may be configured to receive ECG signals 124 and associated time variables 128 denoting the time at which the ECG signal 124 was received. In one or more embodiments, ECG signals 124 may be received from an 8 or lead ECG wherein each lead includes a sensor 132 configured to receive ECG signals 124 from a particular portion of an individual's body. In one or more embodiments, in instances in which a different number of leads, for example, plurality of sensors are 12 leads and system may be only compatible with processing 6 leads, processor 104 may be configured to convert 12 to 6 leads by employing methods described in U.S. Non-provisional application Ser. No. 18/648,250, filed on Apr. 26, 2024, entitled "APPARATUS AND METHOD OF TRAINING A MACHINE-LEARNING MODEL TO GENERATE DETERMINATIONS USING MISMATCHED-CHANNEL SIGNALS" the entirety of which is incorporated herein by reference. In one or more embodiments, ECG data 118 may contain ECG signals 124 from multiple electrodes recorded over a similar time frame. For example, and without limitation, ECG data 118 may include ECG signals 124 received from multiple electrodes over a similar timeframe of 0 to 10 seconds. In one or more embodiments, matrix 120 may include a 2-dimensional array as shown as a non-illustrative example below.

$$M_{ECG} = \begin{bmatrix} [0.1, 0.15, 0.2, 0.25] \\ [-0.1, -0.15, -0.2, -0.25] \\ [0.0, 0.05, 0.1, 0.15] \end{bmatrix}$$

With continued reference to FIG. 1, ECG data 118 may include unlabeled training data. "Unlabeled training data" for the purposes of this disclosure is data that lacks distinct element or classifiers that can be used to train a machine learning model. in an embodiment, unlabeled training data may include data that has not been classified by an individual or computing system. In one or more embodiments, "labeled training data" may refer to data that has been labeled and configured to training machine learning models. in an embodiment, labeled training data may include training data with inputs and correlated outputs. In an embodiment, unlabeled training data may include data that has not been modified to train machine learning models. In one or more embodiments, Unlabeled training data may include data received directly from one or more sensors 132 without modification. In one or more embodiments, unlabeled training data may include data that may be used for training of one or more machine learning models but has not been specifically modified for training of one or more machine learning models. In one or more embodiments, unlabeled training data may lack tags, labels, classifications, correlated outputs and the like. In one or more embodiments, ECG data 118 may contain unlabeled training data wherein ECG data 118 may contain data received directly from one or more sensors 132 and/or leads. Training data may be described in further detail below.

With continued reference 1, processor 108 is configured to create one or more overlapping temporal patches 136 from the plurality of ECG data 118. A "temporal patch" for the purposes of this disclosure refers to a portion of ECG signals 124 over a given period of time. For example, and without limitation, ECG signals 124 may be recorded over a time period of 0 to 100 seconds wherein temporal patch 140 may correspond to ECG signals 124 received from the time interval of 20 seconds to 30 seconds. In an embodiment, temporal patch 140 refers to a segment of ECG data 118 wherein the segment corresponds to a particular time frame or given period of time. In one or more embodiments, Temporal patch 140 may refer to a segment or portion of ECG set wherein the segment includes ECG signals 124 over a particular time frame. in an embodiment, Temporal patch 140 refers to a given set of ECG signals 124 received from one sensor 132 over a given time frame. For example, and without limitation, ECG data 118 may include ECG signals 124 received from leads II, III, V1, V2, V3, V4, wherein temporal patch 140 may include ECG signals 124 from lead II over a particular time frame and/or time period. In one or more embodiments, temporal patch 140 may refer to a portion of ECG signals 124 received from a particular sensor 132, such as for example, a portion of ECG signals 124 received from lead II. "Overlapping temporal patches" for the purposes of this disclosure refer to temporal patches 140 from one or more sensors 132 that correspond to similar time frames. For example, and without limitation, overlapping temporal patches 136 may include a portion of ECG signals 124 associated with Leads II and III wherein the portion of ECG signals 124 correspond to ECG signals 124 received over a period of 10 seconds to 20 seconds. In one or more embodiments, temporal patches 140 may include segments of data received from each sensor 132 that correspond to similar time frames. In one or more embodiments, overlapping temporal patches 136 may correspond to temporal patches 140 from each ECG set that contain similar time variables 128, similar ranges of time variables 128 and the like. in an embodiment, each ECG set may contain ECG signals 124 received from each sensor 132 over a given period of time wherein overlapping temporal patches 136 may include segments of each ECG set corresponding to similar periods of time in which the ECG signals 124 were received. In one or more embodiments, ECG data 118 may include data received from 8 differing leads wherein overlapping temporal patches 136 may include segments of the data over a similar time frame. In one or more embodiments, overlapping temporal patches 136 may include ECG signals 124 received from differing sensors 132 with similar time variables 128. For example, and without limitation, ECG signals 124 associated with time variables 128 ranging from 0 to 10 seconds may include a temporal patch 140, wherein multiple temporal patches 140 with similar time variables 128 may be included in overlapping temporal patches 136. In one or more embodiments, overlapping temporal patches 136 may include temporal patches 140 with similar time variables 128, similar ranges of time variables 128, ECG signals 124 received over similar periods of time and the like. In one or more embodiments, each temporal patch 140 of the overlapping temporal patches 136 includes a segment of voltage signals from each of the one or more leads and/or sensors 132. In one or more embodiments, temporal patches 140 within overlapping temporal patches 136 may be referred to singularly as 'overlapping temporal patch.' In one or more embodiments, overlapping temporal patch may correspond to a singular temporal patch 140 within a plurality of overlapping temporal patches 136.

With continued reference to FIG. 1, ECG signals 124 associated with each sensor 132 may be segmented into multiple temporal patches 140 wherein each temporal patch 140 may correspond to ECG signals 124 over a given period of time. In one or more embodiments, ECG set may be segmented into multiple temporal patches 140. For example, and without limitation, sensor 132 may record ECG signals 124 over a span of 100 seconds wherein each 10 seconds may refer to temporal patch 140. Continuing, multiple sensors 132 may record ECG signals 124 over a span of 100 seconds wherein the first ten seconds of each sensor 132 may be referred to as overlapping temporal patches 136. In one or more embodiments, each ECG set may include information of ECG signals 124 over a given time received from each sensor 132 wherein overlapping temporal patches 136 may include segments of the ECG sets having similar timeframes and/or variables. In one or more embodiments, processor 108 may be configured to create overlapping temporal patches 136 by segmenting ECG data 118 based on time variables 128 wherein for example, ECG signals 124 received from sensors 132 may be segmented into 5 second time frames. In one or more embodiments, each matrix 120 may include ECG signals 124 received from each sensor 132 and corresponding time variables 128. In an embodiment, Matrix 120 may be segmented into temporal patches 140 wherein each temporal patch 140 may contain ECG signals 124 over particular time frame. In one or more embodiments, overlapping temporal patches 136 may include segmented matrices having similar time variables 128 (e.g. similar time periods corresponding to ECG signals 124).

With continued reference to FIG. 1, ECG data 118 and/or ECG sets may be divided and/or segmented into multiple consecutive non-overlapping temporal patches 136 (say P), such that each patch is an array of shape N×(T//P). Therefore, the first patch may contain all N leads with data points coming from time 0 to T//P, the second patch would contain all N leads coming from points T//P to 2T//P, and the like. In one or more embodiments, N may denote the number of leads and T may denote the number of ECG signals 124 and/or voltage signals, wherein T may depend on the frequency of the acquired ECG signal 124 (say f) and the length of the signal in seconds (say S), i.e., T=f*S. In one or more embodiments, an array of N×T may be segmented into multiple overlapping temporal patches 136 wherein each set of overlapping temporal patches 136 may include an array denoted as N×(T//P) wherein P may denote the amount of temporal patches 140 created for each set of ECG signals 124. For example, and without limitation, a value of P such as 3 may indicate that the set of ECG signals 124 is divided into three segments wherein the first segment (i.e., first set of temporal patches 140) may contain a time frame of 0 to T//3, the second segment may contain a time frame of T//3 to 2T//3 and the third segment may contain a timeframe of 2T//3 to 3T//3.

In one or more embodiments, processor 108 may be configured to create one or more overlapping temporal patches 136 as a function of a temporal element 144. A "temporal element" for the purposes of this disclosure is information indicating a time frame associated with each temporal patch 140. For example, and without limitation, temporal element 144 may be 10 seconds wherein each temporal patch 140 may include a series of ECG signals 124 received over the span of 10 seconds. In one or more embodiments, temporal element 144 may include time ranges such as but not limited to ranges of 5 milliseconds (ms), 10 ms, 15 ms, 20 ms, 30 ms, 40 ms, and the like. In one or more embodiments, temporal element 144 may indicate how many segments may be created from a set of ECG signals 124. For example, and without limitation, temporal element 144 may include a number such as '4' wherein 4 may indicate that the ECG signals 124 should be separated into 4 segments. In one or more embodiments, temporal element 144 may indicate how many temporal patches 140 should be created for each set of ECG signals 124 associated with each sensor 132. In one or more embodiments, temporal element 144 may be denoted as 'P' as shown above wherein the numerical value of 'p' may indicate how many segments ECG signals 124 should be split into. For example, and without limitation, a temporal element 144 having a value of 3 may indicate that the ECG signals 124 should be split into 3 segments. In one or more embodiments, Temporal elements 144 may be received as a function of user input wherein an individual interacting and/or associated with system 100 may indicate the amount of overlapping temporal patches 136 to be created. In one or more embodiments, temporal elements 144 may be generated by processor 108. In one or more embodiments, processor 108 may be configured to generate smaller temporal patches 140 wherein smaller temporal patches 140 may indicate ECG signals 124 over a smaller time frame. In one or more embodiments, processor 108 may be configured to generate multiple temporal patches 140 and decrease the amount of temporal patches 140 following each iteration and/or following success of each processing of data. For example, and without limitation a set of ECG signals 124 recorded over a span of 100 seconds may first be split into 20 temporal patches 140 wherein each temporal patch 140 may include ECG signals 124 recorded over a range of 5 seconds. Continuing, processor 108 may be configured to reduce the number of temporal patches 140 wherein on a next iteration, processor 108 may be segment the ECG signals 124 into 10 temporal patches 140 such that each temporal patch 140 includes ECG signals 124 recorded over a range of 10 seconds. in an embodiment, processor 108 may increase or reduce the number of temporal patches 140 in order to train one or more machine learning models as described in this disclosure. In an embodiment, and as described in further detail below, temporal patches 140 may be removed to train machine learning models wherein larger temporal patches 140 may be more difficult to predict whereas smaller temporal patches 140 may be easier for the machine learning model to predict. in an embodiment, processor 108 may increase or decrease temporal element 144 in order to better train the machine learning model as described below.

With continued reference to FIG. 1, each ECG set may contain multiple temporal patches 140. In one or more embodiments, each temporal patch 140 within each ECG set may contain corresponding overlapping temporal patches 136 wherein the overlapping temporal patches 136 are temporal patches 140 from other ECG sets. In one or more embodiments, ECG data 118 may contain multiple sets of overlapping temporal patches 136 wherein each set of overlapping temporal patches 136 may contain a temporal patch 140 from each ECG set with similar time variables 128. For example, and without limitation, a first set of overlapping temporal patches 136 may contain a temporal patch 140 ranging from 0 and 10 seconds in a first ECG set, a first temporal patch 140 ranging from 0 and 10 seconds in a Second ECG set, a first temporal patch 140 ranging from 0 and 10 seconds in a third ECG set and the like. Continuing, a second set of overlapping temporal patches 136 may contain a second temporal patch 140 ranging from 10 and 20 seconds in a first ECG set, a second temporal patch 140 ranging from 10 and 20 seconds in a second ECG set, a second temporal patch 140 ranging from 10 and 20 seconds in a third ECG set and the like. In one or more embodiments, processor 108 may be configured to create sets of overlapping temporal patches 136 wherein each set contains temporal patches 140 from each ECG set with similar time variables 128.

With continued reference to FIG. 1, temporal patches 140 may be consecutive wherein, for example, a first temporal patch 140 may include recorded ECG signals 124 from 0 to 10 seconds, a second temporal patch 140 may include ECG signals 124 from 10 to 20 seconds and the like. In one or more embodiments, processor 108 may be configured to segment Matrix 120 into multiple submatrices wherein each submatrices may contain a portion of Matrix 120.

With continued reference to FIG. 1, processor 108 is configured to mask at least one overlapping temporal patch from the one or more overlapping temporal patches 136. In one or more embodiments, a process of masking temporal patches 140 may include the removal of the information associated with one or more temporal patches 140 from ECG data 118. In one or more embodiments, masking at least one overlapping temporal patch may include the removal of at least one temporal patch 140 from a set of overlapping temporal patches 136. In one or more embodiments, masking at least one temporal patch 140 may include the removal of a set of temporal patches 140 from a plurality of sets of temporal patches 140 within ECG data 118. In one or more embodiments, processor 108 may be configured to randomly remove or obscure temporal patches 140 from each set of temporal patches 136. In one or more embodiments, a plurality of sets of overlapping temporal patches 136 may exist within ECG data 118 wherein processor 108 may configured to mask at least one set of temporal patches 140. In one or more embodiments, processor 108 may remove more than one temporal patches 140 from each set of overlapping temporal patches 136. In one or more embodiments, processor 108 may iteratively remove one or more temporal patches 140 following each iteration of the processing in order to train a machine learning model as will be described in further detail below. In one or more embodiments, processor 108 may be configured to remove temporal patches 140 and/or set of overlapping temporal patches 136 consecutively wherein a first temporal match and/or first set of overlapping temporal patches 136 may be removed, wherein one or more processes (e.g. prediction of masked temporal patches) may be completed, and the first set may be placed back, and a second set removed. In one or more embodiments, a process of masking may include preventing a computing system from asking a particular set of information without removing the information. In one or more embodiments, processor 108 may mask at least one overlapping temporal patch from the one or more overlapping temporal patches 136 by radiantly masking at least one overlapping temporal patch. In one or more embodiments, processor 108 may use pseudorandom number generation in order to generate random numerical value which may correspond to temporal patches 140 to be removed. In one or more embodiments, processor 108 may use true random number generation wherein processor 108 may use atmospheric noise, clock speed, CPU temperature, radioactive decay and the like in order to generate random variables which may be used to select temporal patches 140 and/or overlapping temporal patches 136 to be masked. In one or more embodiments, processor 108 may be configured to mask at least one temporal patch 140 within at least one set of overlapping temporal patches 136. In one or more embodiments, processor 108 may be configured to mask at least one set of overlapping temporal patches 136 from a plurality of sets of overlapping temporal patches 136. In one or more embodiments, a masked temporal patch 148 may be used to train one or more machine learning models as described in further detail below. In one or more embodiments, temporal patches 140 and/or sets of overlapping temporal patches 136 which are masked may be referred to as "masked temporal patches."

With continued reference to FIG. 1, in one or more embodiments, processor 108 may be configured to generate modified ECG data 152. "Modified ECG data" for the purposes of this disclosure is ECG data 118 in which one or more temporal patches 140 have been masked. For example, and without limitation, modified ECG data 152 may lack a particular set of ECG values associated with a particular time frame. In another non limiting example, an ECG set within ECG data 118 may contain missing temporal patches 140. In one or more embodiments, ECG data 118 may contain a multiple set of overlapping temporal patches 136 wherein modified ECG data 152 may lack at least one of the multiple sets of overlapping temporal patches 136. In one or more embodiments, processor 108 may modify ECG data 118 by removing at least one temporal patch 140 and/or at least one set of overlapping temporal patches 136.

With continued reference to FIG. 1, processor 108 is configured to pretrain an ECG machine learning model 156 to predict at least one masked overlapping temporal patch of the one or more overlapping temporal patches 136. In one or more embodiments, computing device 104 may include a machine learning module to implement one or more algorithms or generate one or more machine-learning models to generate outputs. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from database 116, user inputs and/or be provided by a user. In other embodiments, a machine-learning module may obtain a training set by querying a communicatively connected database 116 that includes past inputs and outputs. Training data may include inputs from various types of databases 116, resources, libraries, dependencies and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to categories by tags, tokens, or other data elements. A machine learning module may be used to create a machine learning model and/or any other machine learning model using training data. Training data may be data sets that have already been converted from raw data whether manually, by machine, or any other method. In some cases, the machine learning model may be trained based on user input. For example, a user may indicate that information that has been output is inaccurate wherein the machine learning model may be trained as a function of the user input. In some cases, the machine learning model may allow for improvements to computing device 104 such as but not limited to improvements relating to comparing data items, the ability to sort efficiently, an increase in accuracy of analytical methods and the like.

With continued reference to FIG. 1, in one or more embodiments, a machine-learning module may be generated using training data. Training data may include inputs and corresponding predetermined outputs so that machine-learning module may use the correlations between the provided exemplary inputs and outputs to develop an algorithm and/or relationship that then allows machine-learning module to determine its own outputs for inputs. Training data may contain correlations that a machine-learning process may use to model relationships between two or more categories of data elements. The exemplary inputs and outputs may come from a database 116, and/or be provided by a user. In other embodiments, machine-learning module may obtain a training set by querying a communicatively connected database 116 that includes past inputs and outputs. Training data may include inputs from various types of databases 116, resources, libraries, dependencies and/or user inputs and outputs correlated to each of those inputs so that a machine-learning module may determine an output. Correlations may indicate causative and/or predictive links between data, which may be modeled as relationships, such as mathematical relationships, by machine-learning processes, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. An "ECG machine learning model" for the purposes of this disclosure is a machine learning model configured to receive ECG signals 124 as inputs and output information associated with the ECG signals 124. For example, and without limitation, ECG machine learning model 156 may receive ECG signals 124 and output a predicted disease, a predicted heart abnormality and the like. in an embodiment, ECG machine learning model 156 may be used to predict various cardiac abnormalities that have occurred, are currently occurring and/or will occur in the future based on an individual's current electrocardiogram signals received. ECG machine learning model 156 is described in further detail below.

With continued reference to FIG. 1, processor 108 may be configured to pretrain ECG machine learning model 156. "Pretraining a machine learning model" as referred to herein refers to a computational process in which a machine learning model is trained on a large data set to learn general features or representation before fine tuning the machine learning model for a specific task. For example, and without limitation, pre-training ECG machine learning model 156 may include determining waveform patterns, heart rate variability, and other relevant characteristics of the ECG signals 124 within ECG data 118 and/or modified ECG data 152. In one or more embodiments, pretraining ECG machine learning model 156 may allow for ECG machine learning model 156 to make determinations on unlabeled training data. In one or more embodiments, ECG machine learning model 156 may make determination on modified ECG data 152 such as relevant features, patterns and the like wherein the determinations may be used as training data when fine tuning ECG machine learning model 156 for a particular cardiac related purpose. In one or more embodiments, pretraining ECG machine learning model 156 may allow for unlabeled training data such as ECG data 118 to be used for multiple purposes. For example, and without limitation, ECG data 118 may be used to determine cardiac abnormalities in one machine learning model and used to determine heart diseases in another machine learning model. In one or more embodiments, pretraining a machine learning model may allow for a machine learning model to leverage general knowledge from a broad dataset, such as ECG data 118, in order to better generate outputs using a limited labeled training data set. In one or more embodiments, pretraining ECG machine learning model 156 may allow for determinations of relevant features, patterns and the like within ECG data 118 prior to training ECG machine learning model 156 for a particular and/or specific use. In one or more embodiments, ECG machine learning model 156 may contain labeled training data containing inputs such as ECG signals 124 and correlated disease states, disease classifications and the like. in an embodiment, labeled training data may be used to make determinations about ECG data 118 and create a larger set of training data. In one or more embodiments, pretraining may allow for iterative training of ECG machine learning model 156 absent human input. In an embodiment, processor 108 may be configured to receive ECG signals 124 from patients, and pretrain ECG machine learning model 156 to determine relevant features, patterns and the like. In an embodiment, ECG machine learning model 156 may be pre-trained following receipt of ECG signals 124 from a patient. In one or more embodiments, ECG machine learning model 156 may be iteratively trained with large data sets containing ECG signals 124 such as ECG data 118. In one or more embodiments, pretraining ECG machine learning model 156 may include utilizing an unlabeled training data set such as ECG data 118 to generate its own labels based on the unlabeled training data received.

With continued reference to FIG. 1, pretraining ECG machine learning model 156 includes a process in which ECG machine learning model 156 and/or processor 108 predicts missing, masked temporal patches 148 and/or sets of overlapping temporal patches 136. For example, and without limitation, ECG machine learning model 156 may predict missing temporal patches 140 within modified ECG data 152, wherein ECG machine learning model 156 may compare predictions to the actual information contained within temporal patches 140 and/or sets of overlapping temporal patches 136 as indicated by ECG data 118. In one or more embodiments, ECG machine learning model 156 may be configured to receive modified ECG data 152 wherein ECG machine learning model 156 may be tasked with determining masked portions of modified ECG data 152 such as masked temporal patches 148. In one or more embodiments, ECG machine learning model 156 may be configured with a pretext task using modified ECG data 152. In one or more embodiments, the pretext task may include predicting and/or finding missing temporal patches 140. In one or more embodiments, ECG machine learning model 156 may extract relevant features from modified ECG data 152 in order to predict masked temporal patches 148. In one or more embodiments, ECG machine learning model 156 may contain a redetermined set of values of parameters wherein the parameters refer to weights and biases. In one or more embodiments, parameters may be initialized randomly or received from similar machine learning models. In one or more embodiments, during pretraining, parameters of ECG machine learning model 156 may be given initial values wherein the parameters may change in order to fine tune machine learning model for a specific purpose. In one or more embodiments, pretraining involves modifying parameters before training of the machine learning model based on the input data such as ECG data 118 in order to learn meaningful representations or features that can be further refined further on in order fine tune ECG machine learning model 156 for a specific task. In one or more embodiments, ECG machine learning model 156 may receive as an input modified ECG data 152 and predict masked temporal patches 148. In one or more embodiments, ECG machine learning model 156 may compare predictions of the masked temporal patches 148 to the masked temporal patches 148. In one or more embodiments, ECG machine learning model 156 may utilize a loss function in order to measure the discrepancy between predicted outputs of ECG machine learning model 156 and the actual masked temporal patches 148. In one or more embodiments, ECG machine learning model 156 may adjust parameters iteratively through optimization techniques such as, but not limited to gradient descent to minimize the discrepancy.

In one or more embodiments, a machine learning model such as ECG machine learning model 156 may contain parameter values 160. "Parameter values" for the purposes of this disclosure are internal variables that a machine learning model has generated from training data in order to make predictions. In one or more embodiments, parameter values 160 may be adjusted during training or pretraining in order to minimize a loss function. In one or more embodiments, during training, predicted outputs of the machine learning model are compared to actual outputs wherein the discrepancy between predicted output and actual outputs are measured in order to minimize a loss function. A loss function also known an "error function" may measure the difference between predicted outputs and actual outputs in order to improve the performance of the machine learning model. A loss function may quantify the error margin between a predicted output and an actual output wherein the error margin may be sought to be minimized during the training process. The loss function may allow for minimization of discrepancies between predicted outputs and actual outputs of the machine learning model. In one or more embodiments, the loss function may adjust parameter values 160 of the machine learning model. In one or more embodiments, in a linear regression model, parameter values 160 may include coefficient assigned to each feature and the bias term. In one or more embodiments, in a neural network, parameter values 160 may include weights and biases associated with the connection between neurons or nodes within layers of the network. In one or more embodiments, during training and/or pretraining of the machine learning model parameter values 160 of the machine learning model may be adjusted as a function of at least one predicted masked temporal patch 148 and the at least one masked temporal patch 148. In one or more embodiments, processor 108 may be configured to minimize a loss function by adjusting parameter values 160 of ECG machine learning model 156 based on discrepancies between predicted masked temporal patches 148 and masked temporal patches 148. In one or more embodiments, processor 108 may be configured to iteratively pretrain ECG machine learning model 156, wherein processor 108 may be configured to iteratively receive ECG signals 124 from patients and adjust parameter values 160 of ECG machine learning model 156. In an embodiment, the more ECG data 118 and/or ECG signals 124 received by ECG machine learning model 156, the more accurate the ECG machine learning model 156 may be in predicting masked temporal patches 148. In one or more embodiments, parameter values 160 may correspond to learned features of ECG data 118, such as waveforms, patterns, frequencies and the like.

With continued reference to FIG. 1, pretraining ECG machine learning model 156 may include receiving modified ECG data 152 and predicting and/or recreating masked temporal patches 148. In one or more embodiments, parameter values 160 may be adjusted based on predicted masked temporal patches 148 and masked temporal patches 148. In one or more embodiments, pretraining ECG machine learning model 156 may include pretraining ECG machine learning using a vision transformer neural network 164. In one or more embodiments, processor 108 may utilize vison transformer neural network to recreate masked temporal patches 148 wherein recreated masked temporal patches 148 may be compared to masked temporal patches 148. Vision transformer neural network 164 is a machine learning model that processes images in segments in portions called patches. In a vision transformer neural network 164 may process an image pixel by pixel or by sets of pixels. In one or more embodiments, vision transformer neural networks 164 may utilize a self-attention mechanism in order to weight important parts of an input image when making predictions. In one or more embodiments, vision transformer neural network 164 may predict missing temporal matches of ECG sets similar to an inpainting process in which missing parts of an image are predicted or filled. In one or more embodiments, ECG data 118 may be transformed into an image-like structure in order to be processed by vision transformer neural network 164. In one or more embodiments, ECG data 118 may be converted from a textual format to a format such as a spectrogram, a graph a time-frequency representation and the like. In one or more embodiments, Segments of ECG data 118 may be removed such as temporal patches 140 as described above. In one or more embodiments, modified ECG data 152 may be represented in an image like structure wherein the image like structure may contain missing portions corresponding to the masked temporal patches 148. In one or more embodiments, Vision transformer neural network 164 may receive modified ECG data 152 as an input wherein vision transformer neural network 164 may be configured to predict masked temporal patches 148 in an image-like format, such as in a graphical format. In one or more embodiments, vision transformer neural network 164 may be configured to receive information within a one dimensional format, such as a sequence of signals. In one more embodiments, vision transformer neural network 164 may be configured to adjust inputs to accept the dimensionality of the patch and tweak position embeddings to reflect temporal elements. In one or more embodiments, the visional transformer neural network may utilize self-attention mechanism in order to understand relationships dependencies and the like in the image-like structure of the ECG signals 124. In one or more embodiments, similar to natural language processing, vision transformer neural network 164 may weigh the importance of different parts of an input when making predictions. In one or more embodiments, the input may be transformed into three sets of vectors; a query, a key and a value. The query vector is compared with each key vector in the sequence and the result values are called attention score. These score indicate how relevant each element in the sequence is to the current element being processed. In one or more embodiments, vision transformer neural network 164 may processes sequences of data such as ECG data 118 and/or modified ECG data 152 in order to capture dependencies of the data. The model is then tasked with predicting missing segments such as temporal patches 140 based on the received inputs. In one or more embodiments, vision transformer neural network 164 may utilize inference to infer missing portions of a graphical representation of ECG signals 124. In one or more embodiments, the model may be evaluated based on outputs wherein visions transformer may be trained to generate more accurate outputs, and the like. In one or more embodiments, vision transformer neural network 164 may contain parameter values 160 such as but not limited to weights, biases, positional encodings, attention weights, classifier weights and the like. Weights may include numerical values associated with connections between neurons wherein weights may indicate the strength of the connection. Biases may include additional parameters associated with the neurons in order to provide an offset or shift to output values. Attention weights may include the importance each token should give another token in a sequence. Positional encodings may input about the spatial relationships between token in the input image. Classifier weights may include weights associated with each label. in an embodiment, vision transformer neural network 164 may adjust parameter values 160 in order to minimize a loss function and generate more accurate outputs. In one or more embodiments, parameters may be adjusted to minimize error and/or discrepancies between the models predictions and actual results. In one or more embodiments, processor 108 may be configured to adjust one or more parameter values 160 of the ECG machine learning model 156 as a function of the at least one predicted masked temporal patch 148 and the at least one masked temporal patch 148.

With continued reference to FIG. 1, ECG machine learning model 156 may include a machine learning model configured to receive graphical representations and/or images of ECG signals 124. In one or more embodiments, ECG signals 124 may be received in the form of an image, a graphical representation and/or any other visual depiction. In one or more embodiments, pre training ECG machine learning model 156 may include pre training ECG machine learning model 156 with textual data. In one or more embodiments, Vision transformer neural network 164 may receive ECG data 118 in textual format, construct an image-like structure of ECG data 118 and pre-train ECG machine learning model 156 as a function of the image-like structure. in an embodiment, a machine learning model configured to receive images may be trained with information within a textual format. In one or more embodiments, pre training a machine learning model with textual information may allow for decreased computational power, increased computational efficiency, faster processing, and the like. In one or more embodiments, vision transformer neural network 164 may receive ECG data 118, modify ECG data 118 into an image like structure and generate parameter values 160 indicating relationships and representations between the image-like structures. In one or more embodiments, ECG machine learning model 156 may be iteratively trained with textual information even though ECG machine learning model 156 may be configured to receive images as inputs.

With continued reference to FIG. 1, pretraining ECG machine learning model 156 may include the use of one or more autoencoder models 168. An autoencoder model 168 is a machine learning model used for unsupervised machine learning in which inputs are transformed into compressed form of the input data and the inputs are re-created using the compressed form of data. In one or more embodiments, autoencoder model 168 learns a compressed representation of data wherein autoencoder model 168 may determine relevant features of the data. In one or more embodiments, autoencoder model 168 minimizes reconstruction error by adjusting parameter values 160 in order to recreate the input. In one or more embodiments, autoencoder model 168 may receive as an input ECG data 118 and/or modified ECG data 152 wherein autoencoder model 168 may compress ECG data 118 and attempt to recreate ECG data 118. In one or more embodiments, autoencoder model 168 may learn representations between ECG signals 124 by compressing ECG signals 124 into a lower latent space. In one or more embodiments, compression may include the process of removing noise or unwanted signals to remove excess information from ECG signals 124. In one or more embodiments, autoencoder model 168 may be configured to capture important representation of ECG data 118 during compression wherein ECG models may be reconstructed during decoding. In one or more embodiments, autoencoder model 168 may compare encoded inputs to decoded inputs in order to adjust parameter values 160 of the autoencoder model 168. In one or more embodiments, retraining ECG machine learning model 156 may include training autoencoder model 168 to reduce reconstruction error when reconstructing compressed inputs such as ECG data 118. In one or more embodiments, autoencoder model 168 may capture meaningful representations during compression such as irregular patterns, frequencies and the like. In one or more embodiments, autoencoder model 168 may be used to detect anomalies within ECG data 118 wherein autoencoder model 168 may be trained with ECG data 118 representing regular heart activity such that reconstruction of anomalies may indicate a higher reconstruction error and thereby an issue. In one or more embodiments, autoencoder model 168 may contain an encoding function in which input data is transformed and/or compressed. In one or more embodiments, autoencoder model 168 may contain a decoding function in which input data is recreated from the transformed or compressed data. In one or more embodiments, autoencoder model 168 may be iteratively trained to reduce construction loss wherein construction loss refers to the accuracy of the decoded output in comparison to the input. In one or more embodiments, autoencoder model 168 may capture only those variations in data that are needed to reconstruct the input. For example, and without limitation, autoencoder model 168 may capture only those patterns, frequencies, outliers and the like within a set of ECG signals 124 in order to recreate the set of ECG signals 124. In one or more embodiments, autoencoder model 168 may be used to compare sets of ECG signals 124 wherein ECG signals 124 containing similar patterns, frequencies and the like may indicate some sort of likeness.

With continued reference to FIG. 1, processor 108 may utilize a masked autoencoder technique to train ECG machine learning model 156. A masked autoencoder technique refers to a process in which the input data is modified such that various portions are masked or removed and the autoencoder model 168 is configured to reconstruct the original input data. In one or more embodiments, a masked autoencoder model may be configured to receive an input such as modified ECG data 152 and be configured to reconstruct ECG data 118 and/or the masked temporal patches 148. In one or more embodiments, masked autoencoder model can be used for denoising and/or anomaly detection. In one or more embodiments, masked autoencoder model may be configured to remove noise from ECG signals 124 wherein reconstructed outputs may include the missing portions of the ECG signals 124 as well as the noise removed. In one or more embodiments, masked autoencoder model can further be trained on normal ECG signals 124 and/or abnormal ECG signals 124 in order to whether an ECG signal 124 may be determined to be normal or abnormal. In one or more embodiments, masked autoencoder model may be configured with finding similarities between multiple ECG signals 124 in order to determine similarities between normal and abnormal ECG signals 124. In one or more embodiments, masked autoencoder model may contain one or more parameter values 160 that are sought to be adjusted during training. In one or more embodiments, the parameter values 160 may be used for other machine learning models in order to find similarities between ECG signals 124. In one or more embodiments, parameter values 160 of masked autoencoder model, such as but not limited to model architecture parameters, training parameters, regularization parameters and the like may be iteratively adjusted in order to minimize discrepancies between reconstructed temporal patches 140 and masked temporal patches 148. In one or more embodiments, masked autoencoder model may be configured to reconstruct masked temporal patches 148 based on inputs such as modified ECG data 152 wherein parameter values 160 may be adjusted based on discrepancies between the reconstructed output and masked temporal patches 148. In one or more embodiments, masked autoencoder model may be trained using backpropagation and gradient descent to minimize the reconstruction error between the output of the decoder and the original unmasked temporal patch 148 within ECG data 118.

With continued reference to FIG. 1, ECG machine learning model 156 may be trained based on the size of masked temporal patches 148. In one or more embodiments, temporal variables may be adjusted such that parameter values 160 of ECG machine learning models 156 may account for temporal patches 140 with small ranges of time and larger ranges of time. For example, and without limitation, a temporal patch 140 may contain a time duration of 10 seconds wherein ECG machine learning model 156 may be configured to recreate a temporal patch 140 having a time duration of 10 second. Similarly, temporal patch 140 may contain a time duration of 10 ms wherein ECG machine learning model 156 may be configured to recreate temporal patches 140 having a time duration of 10 ms. in an embodiment, processor 108 May vary temporal variables in order to capture larger predicted outputs as well as smaller and more accurate outputs.

With continued reference to FIG. 1, pretraining ECG machine learning model 156 may include generating parameter values 160 for ECG machine learning model 156. In one or more embodiments, pre training ECG machine learning model 156 may include iteratively varying temporal variables in order to predict smaller or larger temporal patches 140.

With continued reference to FIG. 1, in one or more embodiments processor 108 is configured to train ECG machine learning model 156 as a function of the one or more parameter values 160 and a labeled set of ECG training data. in an embodiment, pre training ECG machine learning model 156 may include generating parameter values 160 wherein the parameter values 160 indicate associations between inputs and outputs. in an embodiment, ECG data 118 and/or modified ECG data 152 may be used to generate and/or modify parameter values 160 wherein parameter values 160 may be used to train ECG machine learning model 156.

With continued reference to FIG. 1, ECG machine learning model 156 may be configured to receive inputs such as ECG signals 124, Sets of ECG signals 124 and the like and output information associated with the ECG signals 124. in an embodiment, outputs may include outputs such as cardiac abnormalities, irregular heart rhythms and the like.

With continued reference to FIG. 1, processor 108 may be configured to train ECG machine learning model 156 as a function of one or more parameter values 160 and a labeled set of training data. A labeled set of training data" or "labeled training data" as referred to herein refers to training data that has been labeled such that the training data contains inputs and correlated labeled outputs. For example, and without limitation, labeled training data may include inputs such as ECG signals 124 and correlated outputs labeling the ECG signals 124 with various cardiac abnormalities, abnormal heart rhythms and the like. In one or more embodiments, labeled training may include inputs such as ECG signals 124 and correlated outputs indicating abnormalities, wave patterns, arrythmia and/or other heart conditions. In one or more embodiments, labeled training data may be generated by a user, $3^{rd}$ party and the like. In one or more embodiments, labeled training data may be received from previous iterations of the processing wherein previously received ECG signals 124 may be given a label through user input in order to increase the amount of labeled training data. In one or more embodiments, labeled training data may be iteratively refined and/or modified in order to ensure that inputs contain correct labels and/or correlated outputs. In one or more embodiments, A set of labeled training data may include labeled training data for a particular purpose associated with heart abnormalities. For example, and without limitation, set of labeled training data may include training data exclusively for classification, training data exclusively for pattern recognition, Training data for predicting previous abnormalities, training data for predicting future abnormalities and the like. In one or more embodiments, labeled set of training data may include an unlabeled set of training data wherein processor 104 may perform a similar process on unlabeled set of training data in order to generate labeled set of training data.

With continued reference to FIG. 1, processor 108 may fine tune a pre trained machine learning model, such as ECG machine leaning model, that has been trained on a large set of unlabeled training data. In one or more embodiments, ECG machine learning model 156 may be pre trained to identify patterns and features within ECG signals 124. In one or more embodiments, processor 108 may feed ECG machine learning model 156 with labeled training data in order to adjust the parameters of ECG machine learning model 156 to generate outputs associated with ECG signals 124. In one or more embodiments, processor 108 may update parameters using one or more back propagation techniques. In one or more embodiments, backpropagation techniques may include a processor 108 feeding error rates through a neural network to make the neural network more accurate. In one or more embodiments, errors between the machine learning models predictions and true labels are used to update the model's weights such as parameter values 160. In one or more embodiments, labeled training data may be used to predict outputs associated with an ECG signal 124 wherein outputs of ECG machine learning model 156 may be compared to the true value of the outputs as indicated by labeled training data. In one or more embodiments, regularization techniques such as dropout of weight decay may be used in order to prevent ECG machine learning model 156 from memorizing the small set of labeled training data. In one or more embodiments, training ECG machine learning model 156 may include fine tuning already generated parameter values 160 for a particular purpose.

In one or more embodiments, processor 108 may use one or more transfer learning processes to train ECG machine learning model 156. In one or more embodiments, fine tuning may include a process in which insights, features, representations and the like generated during a pre-training phase can be used and applied to current machine learning models. For example, and without limitation, representations learned using ECG data 118 may be applied to various machine learning models to generate more accurate outputs. In one or more embodiments, processor 108 may use one or more feature extraction processes to extract high level representations of the data received and use those high level representations as inputs into the new model. In one or more embodiments, transfer learning may allow for learned features to be fine-tuned to a specific task or process. For example, and without limitation, extracted features may include recognizing particular patterns, frequencies and the like wherein said particular patterns and frequencies may be used to identify abnormalities. In one or more embodiments, during transfer learning the new model is initialized from weights, parameter values 160 and the like generated during pre-training. In one or more embodiments, parameter values 160 may then be fine-tuned by introducing a labeled training data set. In one or more embodiments, learned representations may be used to identify abnormalities in ECG signals 124, classify patterns in ECG signals 124 to disease states and the like. In one or more embodiments, pretraining ECG machine learning model 156 may allow for generalization wherein ECG machine learning model 156 may be configured to adapt to new unseen data due to the vast amount of ECG data 118 received. In one or more embodiments, a smaller dataset of Labeled training data may prevent generalization as the machine learning model may not be trained to properly analyze unseen data. In one or more embodiments, pre training ECG machine learning model 156 may allow for generalization. In one or more embodiments, ECG machine learning model 156 may be trained following each iteration of apparatus. In one or more embodiments, a user may iteratively provide feedback in order to train ECG machine learning model 156. In one or more embodiments, ECFG machine learning model may be pretrained using a large data set in order to reduce the training of ECG machine learning model 156. In one or more embodiments, pre training ECG machine learning model 156 may allow for more accurate outputs and as a result, less computational power needed to iteratively train ECG machine learning model 156.

With continued reference to FIG. 1, ECG machine learning model 156 may be configured to receive one or more ECG inputs 172 from a patient and output one or more diagnostic labels 176 associated with the patient. in an embodiment, ECG inputs 172 may include ECG signals 124 received from one or more sensors 132 in contact with the patient. As used in the current disclosure, a "diagnostic label" is a label used describe a specific condition, disorder, or illness that affects an individual's health or heart structure or function. A diagnostic label 176 may be any specific condition, disorder, or illness, specifically associated with the heart. In a non-limiting example, diagnostic labels 176 may be associated with conditions related to the cardiac health such as normal sinus rhythm, atrial fibrillation, myocardial infarction, ventricular tachycardia, bundle branch bloc, arrythmias, ischemic heart disease, heart enlargement, conduction abnormalities, cardiac ischemia, electrolyte imbalances, and the like. Processor 108 may assign a diagnostic label 176 to a patient as function of an ECG input received. In one or more embodiments. ECG training data may contain a plurality of ECG inputs 172 and correlated diagnostic labels 176. In an embodiment, ECG training data may be generated by a user, $3^{rd}$ party or the like. In one or more embodiments, ECG training data may be received from electronic health records containing ECG inputs 172 and correlated diagnostic labels 176.

With continued reference to FIG. 1, ECG inputs 172 may include images of ECG signals 124. In one or more embodiments, processor 108 may be configured to perform image classification using an image classifier wherein processor 108 may be configured to detect various features of ECG inputs 172 and assign diagnostic labels 176 based on the various features. An "image classifier," as used in this disclosure is a machine-learning model, such as a mathematical model, neural net, or program generated by a machine-learning algorithm known as a "classification algorithm," as described in further detail below, that sorts inputs of image information into categories or bins of data, outputting the categories or bins of data and/or labels associated therewith. Image classifier may be configured to output at least a datum that labels or otherwise identifies a set of images that are clustered together, found to be close under a distance metric as described below, or the like. Computing device 104 and/or another device may generate image classifier using a classification algorithm, defined as a process whereby computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. In some cases, processor 108 may use an image classifier to identify a key image in data described in any data described in this disclosure. As used herein, a "key image" is an element of visual data used to identify and/or match elements to each other. An image classifier may be trained with binarized visual data that has already been classified to determine key images in any other data described in this disclosure. "Binarized visual data" for the purposes of this disclosure is visual data that is described in binary format. For example, binarized visual data of a photo may be comprised of ones and zeroes wherein the specific sequence of ones and zeros may be used to represent the photo. Binarized visual data may be used for image recognition wherein a specific sequence of ones and zeroes may indicate a product present in the image. An image classifier may be consistent with any classifier as discussed herein. An image classifier may receive input data (e.g. ECG inputs 172 and/or images of ECG signals 124) described in this disclosure and output a key image with the data. In an embodiment, image classifier may be used to compare visual data in data such as ECG inputs 172 with visual data in another data set. Visual data in another data set may include a plurality of visual data retrieved from database 116. In some cases, image classifier may identify one or more components within ECG input. In some cases, image classifier may classify various vector loops, various cardiac vectors, and the like within ECG input. In one or more embodiments, a particular vector loop, cardiac vector and the like within cardiac image may be associated with a particular diagnostic label 176.

With continued reference to FIG. 1, processor 108 may employ pattern matching techniques to identify specific patterns or abnormalities within the ECG input to generate diagnostic label 176. This can involve comparing specific segments, intervals, or waveforms of the ECG input to detect similarities or differences. Cross-correlation, template matching, or dynamic time warping algorithms may be used for this purpose. Processor 108 may perform statistical analysis on various parameters derived from the ECG input to generate diagnostic label 176. This can involve calculating means, standard deviations, or other statistical measures for specific features or segments of the ECG input. By comparing these statistical parameters, the computer can identify significant differences or similarities between the ECG input and a reference image. In one or more embodiments, ECG machine learning model 156 may include a machine learning model configured to receive images as inputs and output diagnostic labels 176. In one or more embodiments, ECG machine learning model 156 may be trained using ECG data 118 in textual format.

With continued reference to FIG. 1, processor 108 may be configured to create a user interface data structure. As used in this disclosure, "user interface data structure" is a data structure representing a specialized formatting of data on a computer configured such that the information can be effectively presented for a user interface. User interface data structure may include ECG machine learning model 156 and/or any other data as described in this disclosure. In one or more embodiments, user interface data structure may allow for interaction with ECG machine learning model 156 to receive generated outputs.

With continued reference to FIG. 1, processor 108 may be configured to transmit the user interface data structure to a graphical user interface. Transmitting may include, and without limitation, transmitting using a wired or wireless connection, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. Processor 108 may transmit the data described above to database 116 wherein the data may be accessed from database 116. Processor 108 may further transmit the data above to a device display or another computing device 104.

With continued reference to FIG. 1, system 100 may include a graphical user interface (GUI). For the purposes of this disclosure, a "user interface" is a means by which a user and a computer system interact. For example, through the use of input devices and software. In some cases, processor 108 may be configured to modify graphical user interface as a function of the inputs and outputs of ECG machine learning model 156 by populating user interface data structure and visually presenting the data through modification of the graphical user interface. A user interface may include graphical user interface, command line interface (CLI), menu-driven user interface, touch user interface, voice user interface (VUI), form-based user interface, any combination thereof and the like. In some embodiments, a user may interact with the user interface using a computing device 104 distinct from and communicatively connected to processor 108. For example, a smart phone, smart tablet, or laptop operated by the user and/or participant. A user interface may include one or more graphical locator and/or cursor facilities allowing a user to interact with graphical models and/or combinations thereof, for instance using a touchscreen, touchpad, mouse, keyboard, and/or other manual data entry device. A "graphical user interface," as used herein, is a user interface that allows users to interact with electronic devices through visual representations. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in graphical user interface. Persons skilled in the art, upon reviewing the entirety of this disclosure, will be aware of various ways in which a graphical user interface and/or elements thereof may be implemented and/or used as described in this disclosure. In one or more embodiments, graphical user interface may include a graphical visualization of the human heart and various locations as to which attention may be needed.

With continued reference to FIG. 1, system 100 may further include a display device communicatively connected to at least a processor 108. "Display device" for the purposes of this disclosure is a device configured to show visual information. In some cases, display device may include a liquid crystal display (LCD), a cathode ray tube (CRT), a plasma display, a light emitting diode (LED) display, and any combinations thereof. Display device may include, but is not limited to, a smartphone, tablet, laptop, monitor, tablet, and the like. Display device may include a separate device that includes a transparent screen configured to display computer generated images and/or information. In some cases, display device may be configured to visually present one or more data through GUI to a user, wherein a user may interact with the data through GUI. In some cases, a user may view GUI through display.

With continued reference to FIG. 1, system 100 may include and/or be included within a mobile unit. "Mobile unit" for the purposes of this disclosure is a device that is capable of being transported from one location to another. In one or more embodiments, mobile unit may include wheels that allow mobile unit to be moved from one location to another. In one or more embodiments, display device may be located atop mobile unit wherein a user may navigate mobile unit with display device around a room. In one or more embodiments, mobile unit may contain a battery pack wherein computing device 104 may be powered by battery back. In one or more embodiments, battery pack may be rechargeable. In one or more embodiments, one or more processes as described above, such as but not limited to processing relating to machine learning models, may be computed on a cloud, network server and the like to save on battery power. In one or more embodiments, mobile unit may allow for system to be navigated throughout an operating room. In one or more embodiments, location of mobile unit may differ for each patient and/or procedure. In one or more embodiments, sensors 132 as described above may be connected to mobile unit wherein mobile unit may be navigated closer to and/or further away from patient based on the location of sensors 132. In one or more embodiments, sensors 132 may contain wiring that needs to be physically connected to mobile unit. In one or more embodiments, mobile unit may allow for movement of system from one location to another in instances in which movement may be needed. In one or more embodiments, mobile unit may allow for receipt of ECG inputs 172 from a patient in order to generate diagnostic labels 176.

Figure 2A:
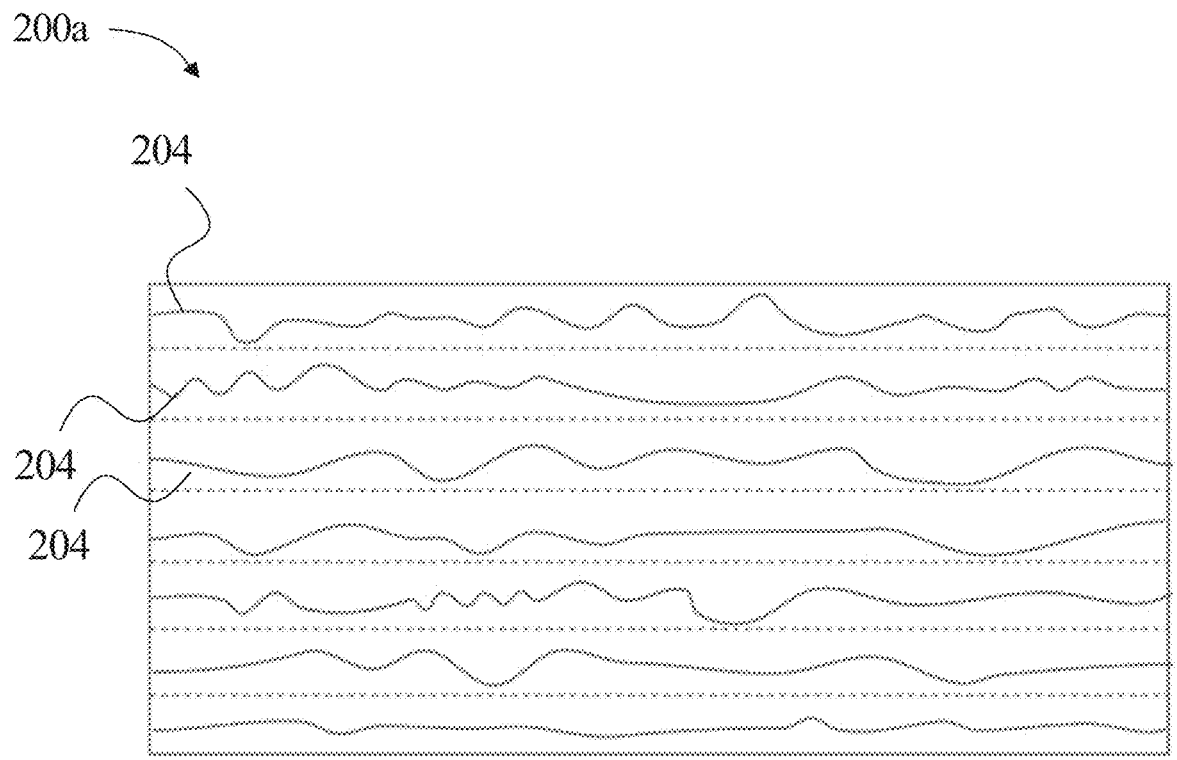
FIGS. 2A-B illustrate a schematic of electrocardiogram signals in accordance with the subject disclosure.

Referring now to FIG. 2A, an exemplary embodiments of a schematic 200a of ECG signals is described. In one or more embodiments, schematic 200a may include a graphical representation of ECG signals 204 as described above. In one or more embodiments, graphical representation may include voltage signals over a given period of time. In one or more embodiments, Schematic may depict ECG signals 204 graphed over a particular period of time. In one or more embodiments, multiple ECG signals 204 may be depicted within a single schematic wherein the amount of ECG signals 204 within the schematic may be refer to 'N' as described above in reference to FIG. 1. In one or more embodiments, schematic 200a may depict a graphical representation of ECG data (as described in reference to FIG. 1).

Figure 2B:
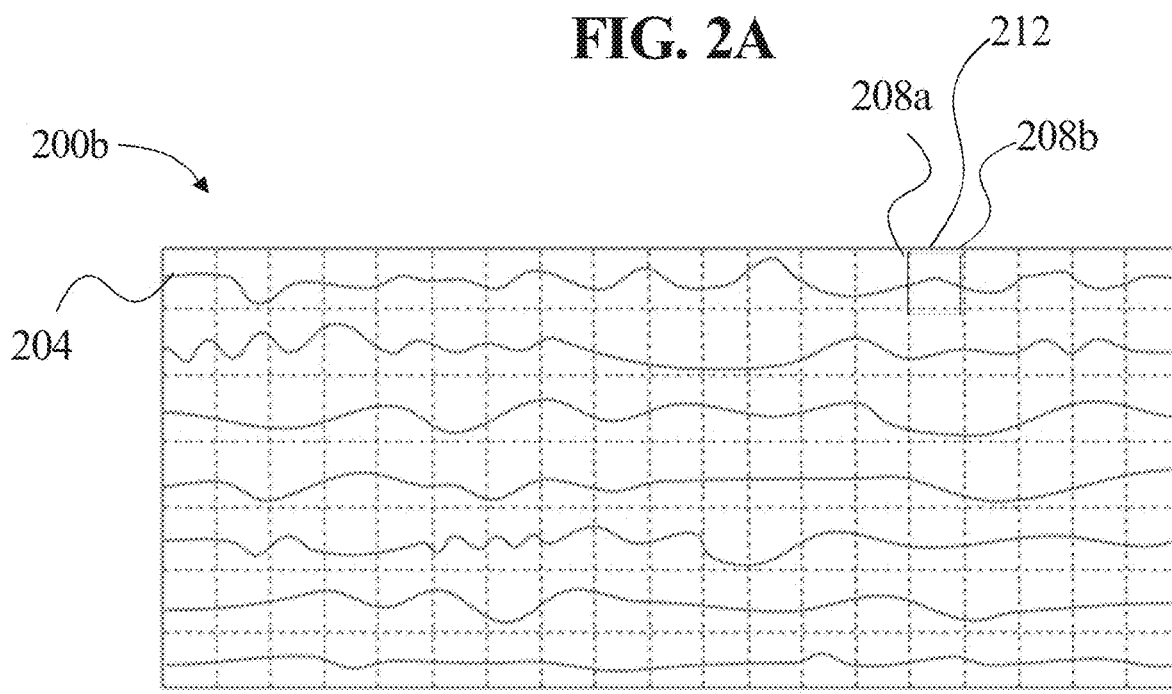

Referring now to FIG. 2B, an exemplary embodiment of a schematic 200b of ECG signals is described. In one or more embodiments, ECG signals may be divided into temporal patches 212 (as described above) wherein a temporal patch 212 may refer to ECG signals from a first boundary 208a to a second boundary 208b. In one or more embodiments, each set of ECG signals 204 may be divided into evenly distributed temporal patches 212 wherein each temporal patch 212 may include ECG signals from a first boundary 208a to a second boundary 208b. In one or more embodiments, ECG signals 208 may be divided into multiple boundaries wherein ECG signals between each boundary may be referred to as temporal patches 212 as described above. In one or embodiments, ECG signals from differing leads within the same boundaries may be referred to as overlapping temporal patches 212. For example, and without limitation, a first ECG signal between first boundary 208a and second boundary 208b, and a second ECG signal between first boundary and second boundary 208b may be referred to as overlapping temporal patches 212. In one or more embodiments, overlapping temporal patches 212 may include ECG signals received from different leads located on an individual's body with similar time frames as indicated by their boundaries. For example, and without limitation, overlapping ECG signals may include ECG signals received from a Lead I and Lead III from a range of 10 ms to 20 ms. In one or more embodiments, the distance between boundaries 208a-b may be referred to as temporal patches 212 wherein each ECG signal may contain multiple consecutive temporal patches 212. In one or more embodiments, boundaries may be created as function of time, wherein a processor may denote to create boundaries at 10 ms intervals such that a first boundary is created at 10 ms, a second boundary is created at 20 ms, a third boundary at 30 ms and the like. In one or more embodiments, temporal patches 212 may be defined as the time frame between a particular pair of boundaries for each ECG signal 204.

Figure 3A:
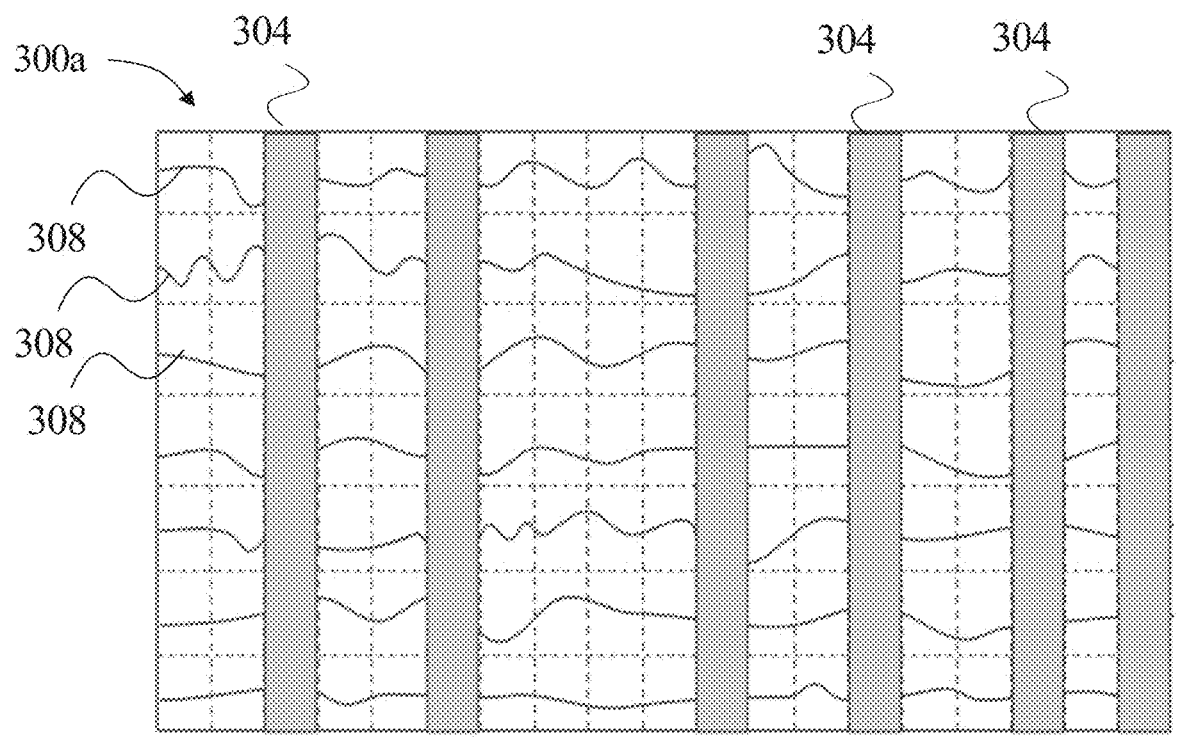
FIG. 3A illustrated a schematic of the electrocardiogram signals with missing portions in accordance with the subject disclosure.

Referring now to FIG. 3A, a schematic 300a of ECG signals with missing portions is described. In one or more embodiments, pre training a machine learning model, such as ECG machine learning model as described above may include the removal of overlapping temporal patches 304a from a set of ECG signals 308. In one or more embodiments, a processor of pretraining may include the creation of boundaries and/or temporal patches as described in reference to FIGS. 2A-2B. In one or more embodiments, pre training ECG machine learning model may include masking overlapping temporal patches 304. In one or more embodiments, overlapping temporal patches may include ECG signals from differing leads that are captured over similar time frames. In one or more embodiments, multiple sets of overlapping temporal patches may exist wherein each set of overlapping temporal patches may correspond to ECG signals 308 received from each lead having similar time frames. For example, and without limitation, a first set of overlapping temporal patches may include ECG signals ranging from 10 ms to 20 ms from 8 differing leads, and a second set of overlapping temporal patches may include ECG signals ranging from 10 ms to 20 ms. In one or more embodiments, each set of overlapping temporal patches may include a single temporal patch from each lead or sensor. In one or more embodiments, pre training ECG machine learning model may include masking entire sets of overlapping temporal patches 308 and/or masking or hiding individual temporal patches within each set of temporal patches 308. As shown in FIG. 3A for illustrative purposes, multiple set of overlapping temporal patches have been masked. In one or more embodiments, schematic 300a may refer to modified ECG data as described above.

Figure 3B:
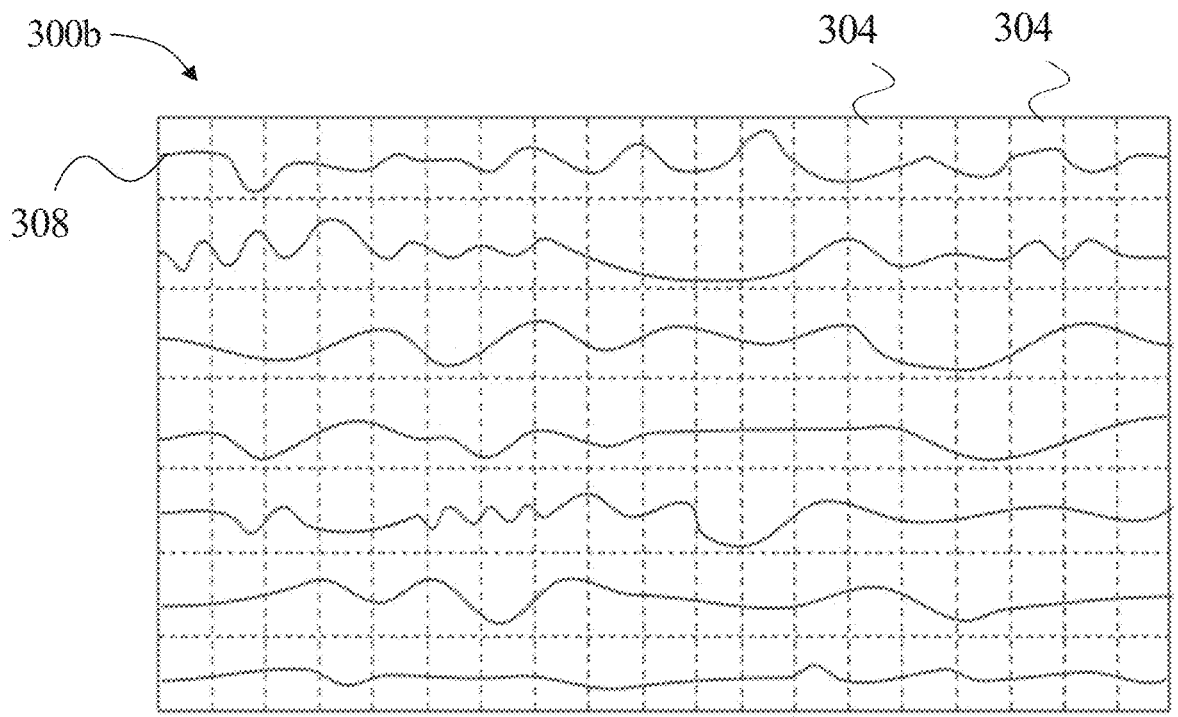
FIG. 3B is a reconstructed schematic of the electrocardiogram signals in accordance with the subject disclosure.

Referring now to FIG. 3B, a reconstructed schematic 300b is described. In one or more embodiments, reconstructed schematic 300a may include predicted outputs of a vision transformer neural network, an autoencoder model and the like. In one or more embodiments, a vision transformer neural network and/or autoencoder model may receive data as depicted in schematic 300a in order to recreate reconstructed schematic 300b. In one or more embodiments, reconstructed schematic 300b may include predicted outputs of one or more machine learning models as described. In one or more embodiments, elements of ECG signals may be masked as depicted in FIG. 3A, wherein a machine learning model may be configured to predict outputs in order to generate ECG signals similar to that of FIGS. 2A-2B. In one or more embodiments, pretraining the machine learning model may include comparing reconstructed schematic 300b to schematic 200a. In one or more embodiments, parameter values of the machine learning model may be adjusted until ECG signals within schematic 300b are similar to that of schematic 200a. In one or more embodiments, a graphical representation of ECG signals 300a as shown in FIGS. 2-3 may be created in order to train a visual transformer neural network. In one or more embodiments, ECG signals may be transformed into an image-like structure prior to utilizing vision transformer neural network in order to train the machine learning model to process images. In an embodiments, training data containing images may require vast amount of data storage and increased computational power while the use of ECG data to generate image like structures may require less computation power and may increase the accuracy of output. In one or more embodiments overlapping temporal patches 304 may be reconstructed and/or predicted as illustrated in FIG. 3B.

Figure 4:
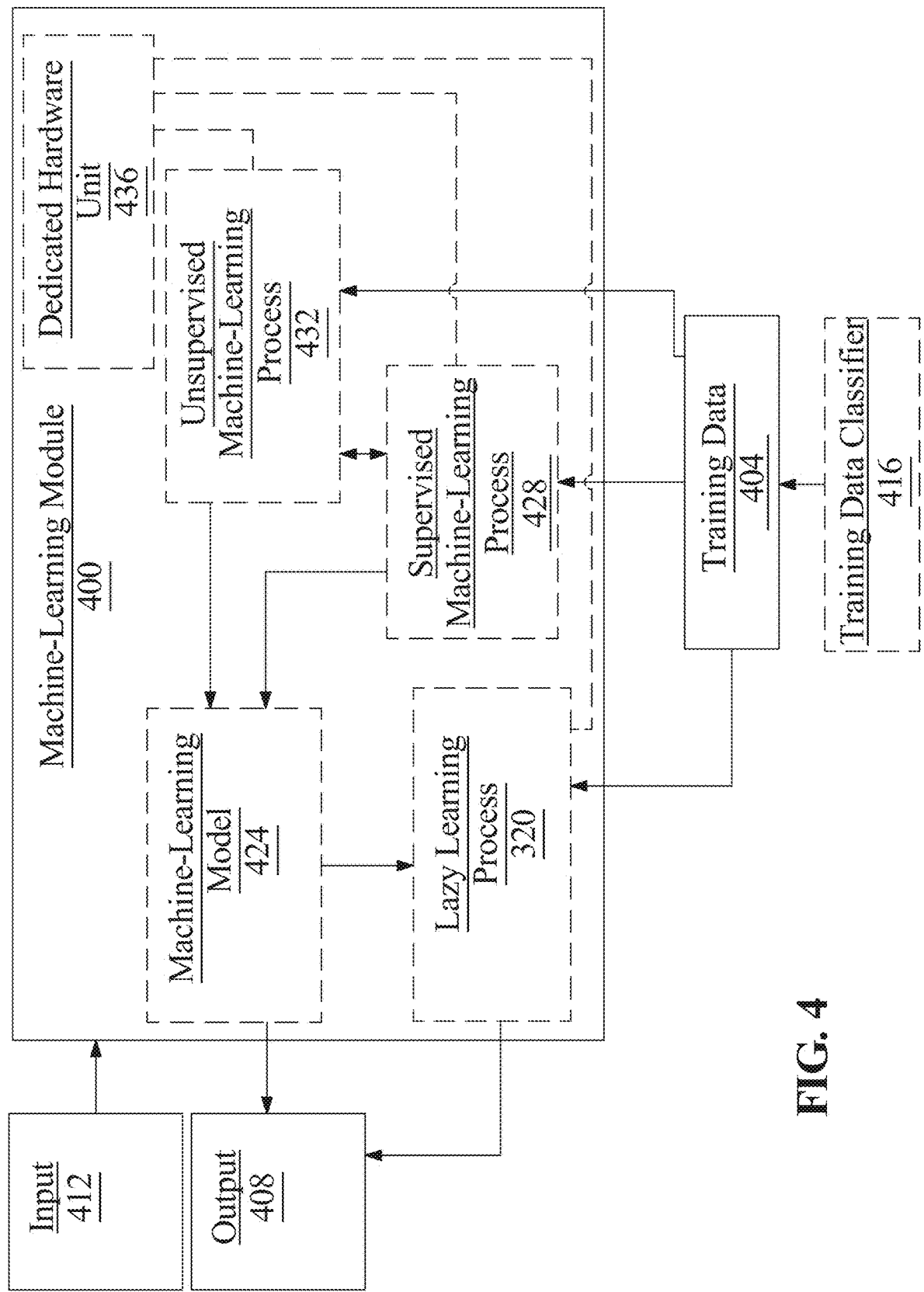
FIG. 4 is a block diagram of an exemplary machine-learning process.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm instantiated in hardware or software logic, data structures, and/or functions that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example inputs may include inputs such as ECG data, modified ECG data, and/or ECG inputs, wherein outputs may include masked temporal patches, parameter values and/or diagnostic labels.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to particular leads that receive ECG data. for example, and without limitation ECG signals may be classified to the lead in which they were received.

Still referring to FIG. 4, computing device 404 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P (B/A) P(A)=P (B), where P(A/B) is the probability of hypothesis A given data B also known as posterior probability; P (B/A) is the probability of data B given that the hypothesis A was true; P(A) is the probability of hypothesis A being true regardless of data also known as prior probability of A; and P (B) is the probability of the data regardless of the hypothesis. A naïve Bayes algorithm may be generated by first transforming training data into a frequency table. Computing device 404 may then calculate a likelihood table by calculating probabilities of different data entries and classification labels. Computing device 404 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 4, computing device 404 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 4, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 4, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 4, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 4, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 4, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness.

Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 4, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 4, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Antialiasing and/or anti-imaging filters, and/or low-pass filters, may be used to clean up side-effects of compression.

Further referring to FIG. 4, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max} : X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 4, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs may include inputs such as ECG data, modified ECG data, and/or ECG inputs, wherein outputs may include masked temporal patches, parameter values and/or diagnostic labels as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

With further reference to FIG. 4, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 4, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 432 may not require a response variable; unsupervised processes 432 may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 4, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 4, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 4, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 4, one or more processes or algorithms described above may be performed by at least a dedicated hardware unit 436. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 436 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 436 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 436 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 5:
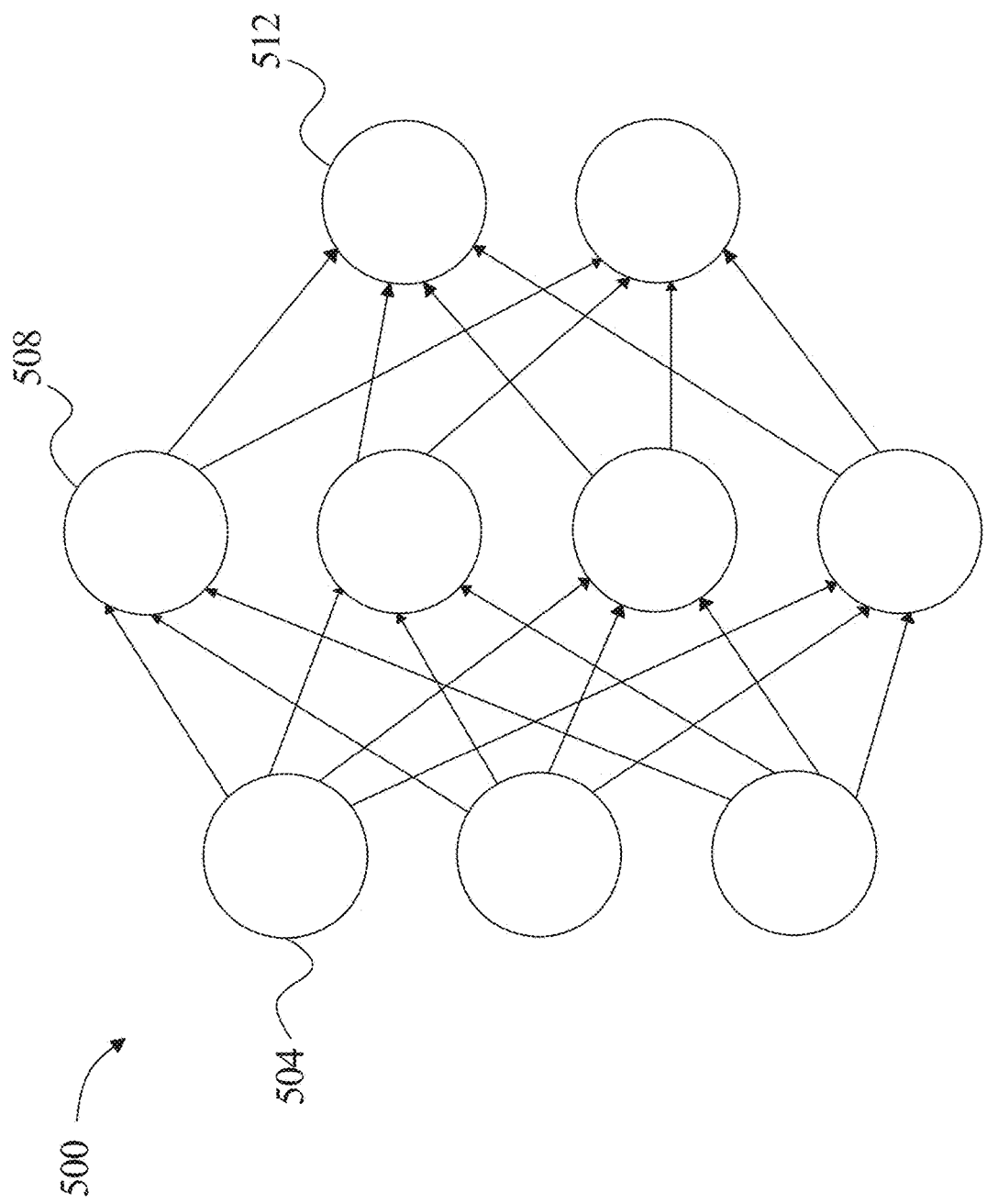
FIG. 5 is a diagram of an exemplary embodiment of a neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
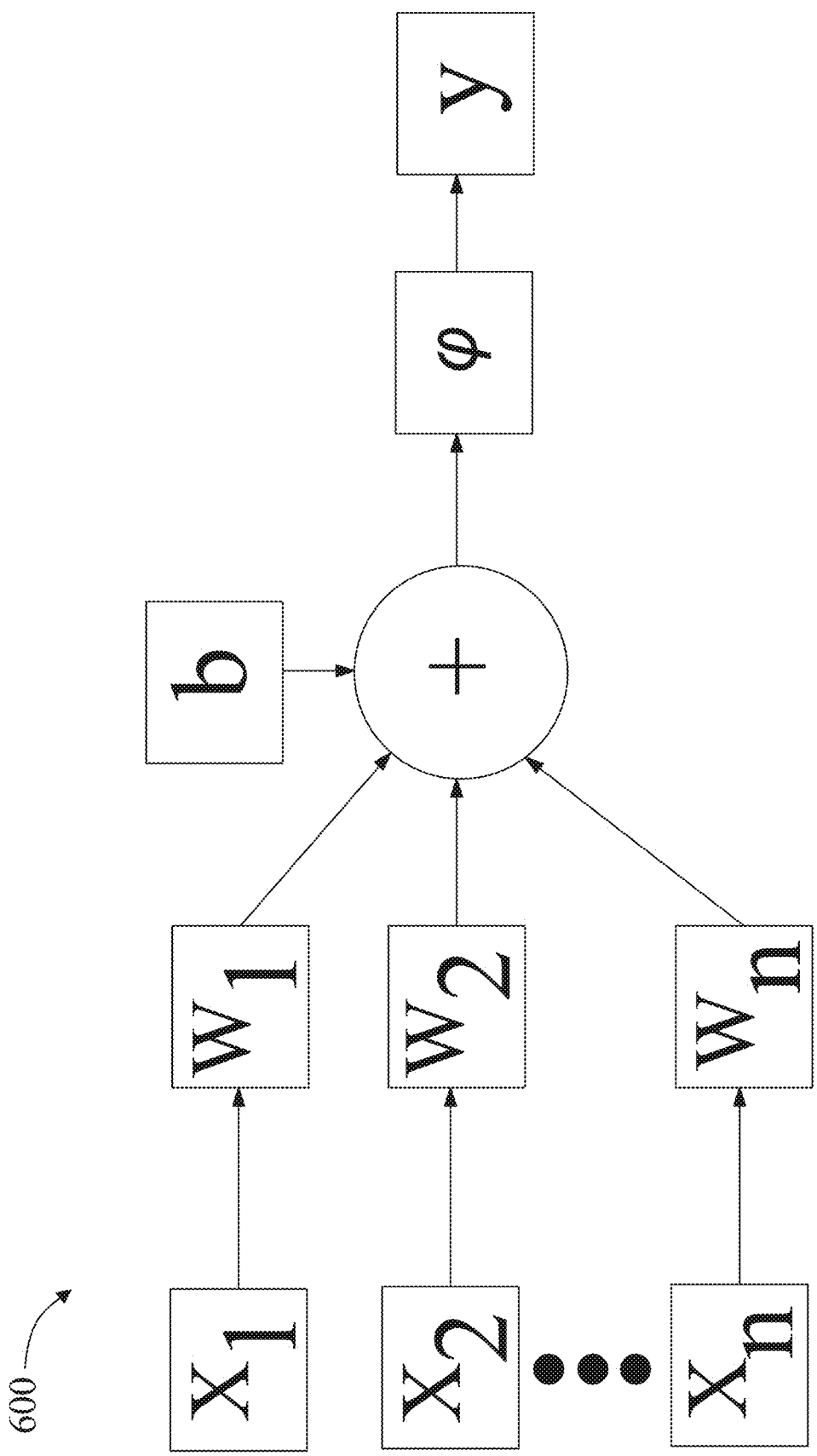
FIG. 6 is a diagram of an exemplary embodiment of a node of a neural network.

Referring now to FIG. 6, an exemplary embodiment of a node 600 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0,x)$, a "leaky" and/or "parametric" rectified linear unit function such as $f(x)=\max(ax,x)$ for some a, an exponential linear units function such as $$f(x) = \begin{cases} x & \text{for } x \leq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 7:
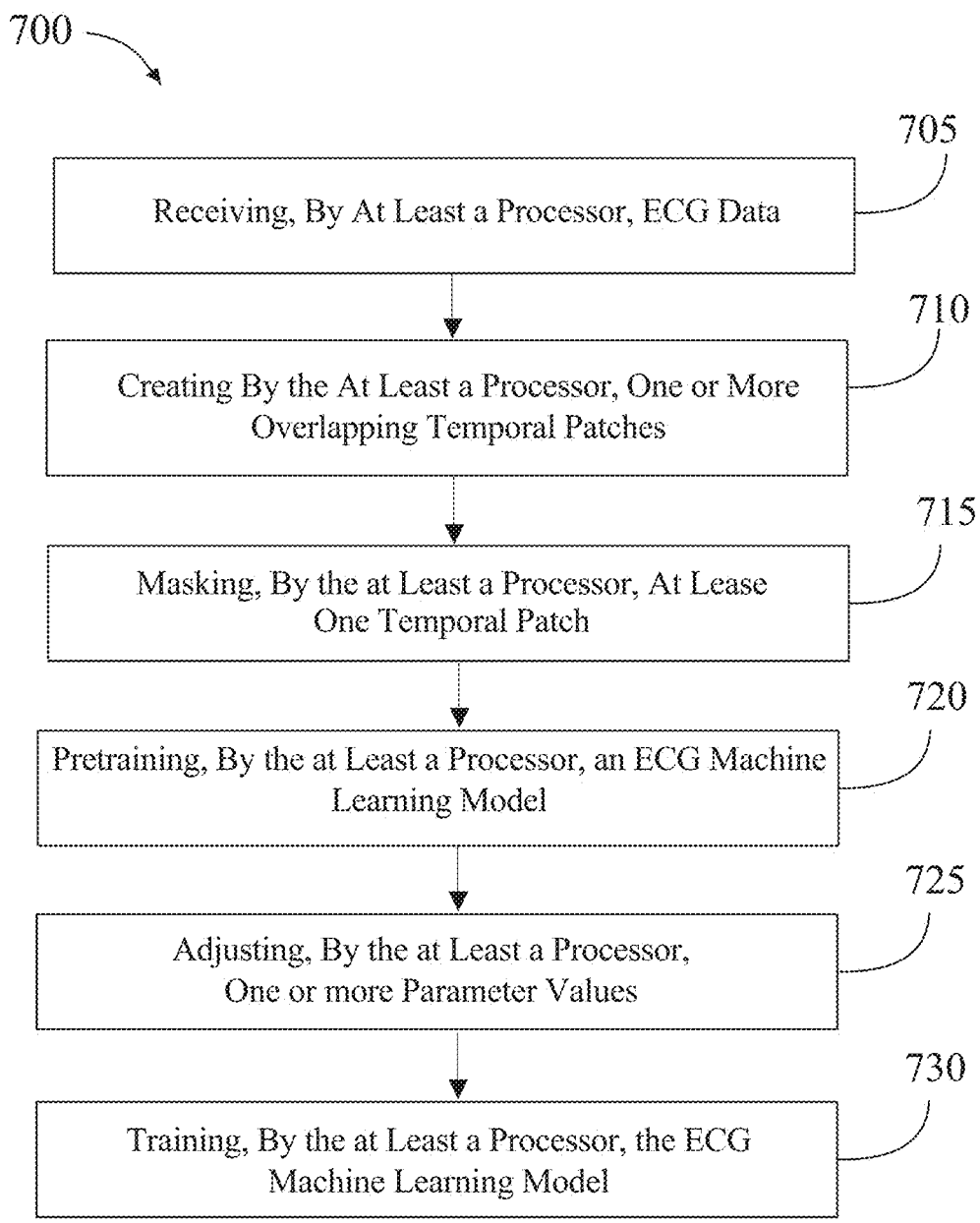
FIG. 7 is a flow diagram illustrating an exemplary embodiment of a method for training machine learning models with unlabeled electrocardiogram signals in accordance with the subject disclosure.

Referring now to FIG. 7, an exemplary method 700 for training machine learning models with unlabeled electrocardiogram (ECG) signals is described. At step 705, method 700 includes receiving, by at least a processor, a plurality of electrocardiogram (ECG) data in a textual format. In one or more embodiments, the plurality of ECG data included unlabeled training data. In one or more embodiments, the plurality of ECG data comprises a matrix comprising one or more leads and voltage signals associated with the one or more leads. In one or more embodiments, receiving, by the at least a processor, the plurality of electrocardiogram (ECG) signals in a textual format includes receiving the plurality of ECG data from a plurality of sensors connected to a plurality of patients. This may be implemented with reference to FIGS. 1-7 and without limitation.

With continued reference to FIG. 7, at step 710 method 700 includes creating, by the at least a processor, one or more overlapping temporal patches from the plurality of ECG data. In one or more embodiments, creating, by the at least a processor, the one or more overlapping temporal patches from the plurality of ECG data includes segmenting the one or more ECG data as a function of a temporal element. In one or more embodiments, each of the one or more overlapping temporal patches includes a segment of the voltage signals from each of the one or more leads. This may be implemented with reference to FIGS. 1-7 and without limitation.

With continued reference to FIG. 7, ate step 715, method 700 includes masking, by the at least a processor, at least one temporal patch from the one or more overlapping temporal patches. In one or more embodiments, masking, by the at least a processor, the at least one temporal patch from the one or more overlapping temporal patches includes randomly masking the at least one temporal patch. This may be implemented with reference to FIGS. 1-7 and without limitation.

With continued reference to FIG. 7, at step 720 method 700 includes pretraining, by the at least a processor, an ECG machine learning model to predict the at least one masked temporal patch from the one or more overlapping temporal patches. In one or more embodiments, pretraining, by the at least a processor, the ECG machine learning model to predict the at least one masked temporal patch from the one or more overlapping patches includes pretraining the ECG machine learning using a vision transformer neural network. In one or more embodiments, pretraining, by the at least a processor, the ECG machine learning model to predict the at least one masked temporal patch from the one or more overlapping temporal patches includes pretraining the ECG machine learning using a masked autoencoder model. In one or more embodiments, the ECG machine learning model is configured to receive one or more ECG inputs from a patient and output one or more cardiac deviations associated with the patient. This may be implemented with reference to FIGS. 1-7 and without limitation.

With continued reference to FIG. 7, at step 725, method 700 includes adjusting, by the at least a processor, one or more parameter values of the ECG machine learning model as a function of the at least one predicted masked temporal patch and the at least one masked temporal patch. This may be implemented with reference to FIGS. 1-7 and without limitation.

With continued reference to FIG. 7, ate step 730 method 700 includes training, by the at least a processor, the ECG machine learning model as a function of the one or more parameter values and a labeled set of ECG training data. This may be implemented with reference to FIGS. 1-7 and without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
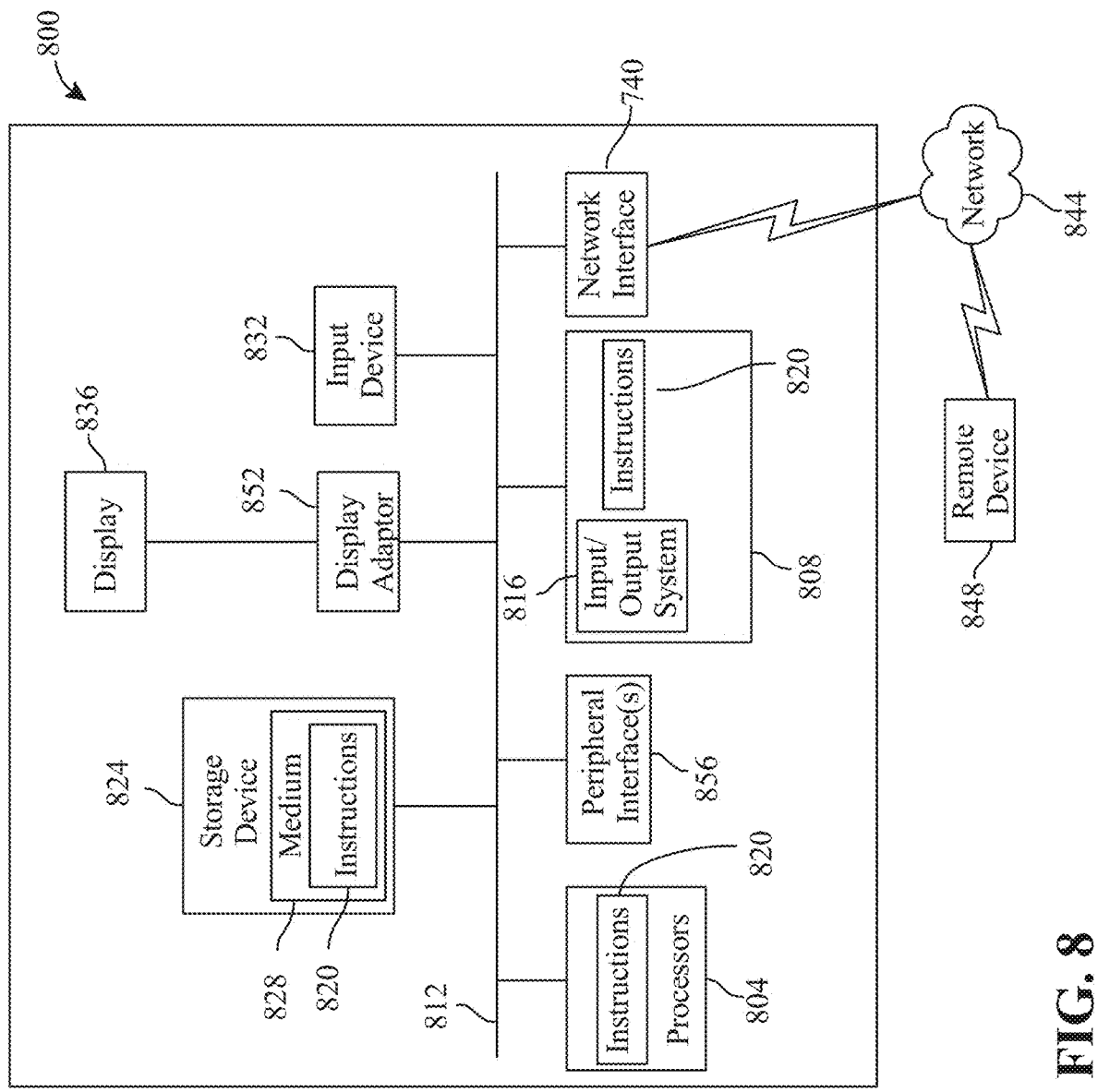
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for training machine learning models with unlabeled electrocardiogram signals, the system comprising:
   at least a processor; and
   a memory communicatively connected to the at least a processor, wherein the memory contains instructions configurating the at least a processor to:
      receive a plurality of electrocardiogram (ECG) data in a textual format;
      create one or more overlapping temporal patches from the plurality of ECG data;
      mask at least one temporal patch from the one or more overlapping temporal patches;
      pretrain an ECG machine learning model to predict the at least one masked temporal patch from the one or more overlapping temporal patches, wherein pretraining the ECG machine learning model to predict the at least one masked temporal patch from the one or more overlapping temporal patches comprises pretraining the ECG machine learning using a masked autoencoder model, wherein the masked autoencoder model is configured to receive modified ECG data and reconstruct ECG data, including the masked temporal patches, to remove noise from the ECG signals by identifying reconstruction errors and adjusting for discrepancies, wherein the masked autoencoder model iteratively adjusts parameter values to minimize differences between the reconstructed temporal patches and the masked temporal patches;
      adjust one or more parameter values of the ECG machine learning model as a function of the at least one predicted masked temporal patch and the at least one masked temporal patch; and
      train the ECG machine learning model as a function of the one or more parameter values and a labeled set of ECG training data.

2. The system of claim 1 wherein the plurality of ECG data comprise unlabeled training data.

3. The system of claim 1, wherein the plurality of ECG data comprises a matrix comprising one or more leads and one or more voltage signals associated with the one or more leads.

4. The system of claim 1, wherein creating the one or more overlapping temporal patches from the plurality of ECG data comprises segmenting the plurality of ECG data as a function of a temporal element.

5. The system of claim 1, wherein pretraining the ECG machine learning model to predict the at least one masked temporal patch from the one or more overlapping patches comprises pretraining the ECG machine learning using a vision transformer neural network.

6. The system of claim 1, wherein receiving the plurality of electrocardiogram (ECG) signals in a textual format comprises receiving the plurality of ECG data from a plurality of sensors attached to a plurality of patients.

7. The system of claim 1, wherein masking the at least one temporal patch from the one or more overlapping temporal patches comprises randomly masking the at least one temporal patch.

8. The system of claim 3, wherein each of the one or more overlapping temporal patches comprises a segment of the voltage signals from each one of the one or more leads.

9. The system of claim 6, wherein the ECG machine learning model is configured to receive one or more ECG inputs from the plurality of sensors attached to a patient and output one or more cardiac deviations associated with the patient.

10. A method for training machine learning models with unlabeled electrocardiogram signals, the method comprising:
    receiving, by at least a processor, a plurality of electrocardiogram (ECG) data in a textual format;
    creating, by the at least a processor, one or more overlapping temporal patches from the plurality of ECG data;
    masking, by the at least a processor, at least one temporal patch from the one or more overlapping temporal patches;
    pretraining, by the at least a processor, an ECG machine learning model to predict the at least one masked temporal patch from the one or more overlapping temporal patches, wherein pretraining the ECG machine learning model to predict the at least one masked temporal patch from the one or more overlapping temporal patches comprises pretraining the ECG machine learning using a masked autoencoder model, wherein the masked autoencoder model is configured to receive modified ECG data and reconstruct ECG data, including the masked temporal patches, to remove noise from the ECG signals by identifying reconstruction errors and adjusting for discrepancies, wherein the masked autoencoder model iteratively adjusts parameter values to minimize differences between the reconstructed temporal patches and the masked temporal patches;
    adjusting, by the at least a processor, one or more parameter values of the ECG machine learning model as a function of the at least one predicted masked temporal patch and the at least one masked temporal patch; and
    training, by the at least a processor, the ECG machine learning model as a function of the one or more parameter values and a labeled set of ECG training data.

11. The method of claim 10 wherein the plurality of ECG data comprise unlabeled training data.

12. The method of claim 10, wherein the plurality of ECG data comprises a matrix comprising one or more leads and one or more voltage signals associated with the one or more leads.

13. The method of claim 10, wherein creating, by the at least a processor, the one or more overlapping temporal patches from the plurality of ECG data comprises segmenting the plurality of ECG data as a function of a temporal element.

14. The method of claim 10, wherein pretraining, by the at least a processor, the ECG machine learning model to predict the at least one masked temporal patch from the one or more overlapping patches comprises pretraining the ECG machine learning using a vision transformer neural network.

15. The method of claim 10, wherein receiving, by the at least a processor, the plurality of electrocardiogram (ECG) signals in a textual format comprises receiving the plurality of ECG data from a plurality of sensors attached to a plurality of patients.

16. The method of claim 10, wherein masking, by the at least a processor, the at least one temporal patch from the one or more overlapping temporal patches comprises randomly masking the at least one temporal patch.

17. The method of claim 12, wherein each of the one or more overlapping temporal patches comprises a segment of the voltage signals from each one of the one or more leads.

18. The method of claim 15, wherein the ECG machine learning model is configured to receive one or more ECG inputs from the plurality of sensors attached to a patient and output one or more cardiac deviations associated with the patient.

* * * * *